(12) United States Patent
Yonemura et al.

(10) Patent No.: US 8,990,028 B2
(45) Date of Patent: Mar. 24, 2015

(54) FRACTURE PREDICTION METHOD, DEVICE, A PROGRAM ARRANGEMENT AND COMPUTER-ACCESSIBLE MEDIUM THEREFOR

(75) Inventors: Shigeru Yonemura, Chiba (JP); Akihiro Uenishi, Chiba (JP); Shunji Hiwatashi, Chiba (JP); Hiroshi Yoshida, Chiba (JP); Tohru Yoshida, Chiba (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 792 days.

(21) Appl. No.: 12/278,117

(22) PCT Filed: Feb. 1, 2007

(86) PCT No.: PCT/JP2007/051711
§ 371 (c)(1),
(2), (4) Date: Aug. 1, 2008

(87) PCT Pub. No.: WO2007/088935
PCT Pub. Date: Aug. 9, 2007

(65) Prior Publication Data
US 2009/0177417 A1    Jul. 9, 2009

(30) Foreign Application Priority Data
Feb. 1, 2006 (JP) .................................. 2006-024975
Feb. 1, 2006 (JP) .................................. 2006-024976

(51) Int. Cl.
*G01L 1/00* (2006.01)
*G01N 3/00* (2006.01)
*G06F 17/50* (2006.01)

(52) U.S. Cl.
CPC .............. *G01N 3/00* (2013.01); *G06F 17/5018* (2013.01); *G06F 17/5095* (2013.01); *G01N 2203/006* (2013.01)
USPC .................................. 702/42; 702/35; 702/43

(58) Field of Classification Search
CPC ............ G01N 3/00; G01N 3/02; G01N 3/08; G01N 3/28; G01N 2203/00; G01N 2203/0003; G01N 2203/0016–2203/0017; G01N 2203/006; G01N 2203/0067; G01N 2203/0069; G01N 2203/0075; G06F 17/50; G06F 17/5009; G06F 17/5018
USPC ................................................ 702/35, 42–43
See application file for complete search history.

(56) References Cited

U.S. PATENT DOCUMENTS 4,852,397 A * 8/1989 Haggag .............................. 73/82
5,232,661 A * 8/1993 Matsuo et al. ................. 420/421
(Continued)

FOREIGN PATENT DOCUMENTS

JP       09279233 A  * 10/1997
JP    2005283130 A  * 10/2005 ............... G01N 3/28
(Continued)

OTHER PUBLICATIONS

Knapp et al., Evaluating Mechanical Properties of Thin Layers Using Nanoindentation and Finite-Element Modeling: Implanted Metals and Deposited Layers, 1996, MRS, Symposium A, SAND-96-1682C, pp. 1-9.*

(Continued)

*Primary Examiner* — Mischita Henson
(74) *Attorney, Agent, or Firm* — Birch, Stewart, Kolasch & Birch, LLP

(57) ABSTRACT

According to exemplary embodiments of the present invention, using a fracture limit stress line obtained by converting a hole expansion ratio into a stress as a criterion for a fracture, the risk of fracture in a material can be evaluated quantitatively by comparing the relationship between data obtained from a numerical analysis using a finite element method and the fracture limit stress line. Thus, when determining a fracture limit in a stretch flange portion in a thin plate in a process including one or more deformation path variations, it is possible to obtain the fracture limit curve easily and efficiently and predict the fracture with high accuracy, and the risk of fracture upon press forming or crash can be evaluated.

23 Claims, 25 Drawing Sheets

(56) References Cited

U.S. PATENT DOCUMENTS

| | | | |
|---|---|---|---|
| 6,555,182 B1* | 4/2003 | Tonosaki et al. | 427/525 |
| 2002/0077795 A1* | 6/2002 | Woods et al. | 703/6 |
| 2004/0011119 A1* | 1/2004 | Jardret et al. | 73/81 |
| 2004/0148143 A1* | 7/2004 | Deobald et al. | 703/2 |
| 2007/0185694 A1* | 8/2007 | Rousselier et al. | 703/2 |
| 2008/0004850 A1* | 1/2008 | Wang | 703/13 |

FOREIGN PATENT DOCUMENTS

| | | |
|---|---|---|
| JP | 08-339396 | 12/2006 |
| WO | WO 2005015167 A1 * | 2/2005 |

OTHER PUBLICATIONS

Milne et al., Comprehensive Structural Integrity, 2003, Elsevier, vols. 1-10, ISBN 978-0-08-043749-1, pp. 655-671.*

Ling, Yun, "Uniaxial True Stress-Strain after Necking", Jun. 1996, AMP Journal of Technology, vol. 5, pp. 37-48.*

Storen, S. and Rice J.R., "Localized Necking in Thin Sheets", 1975, Pergamon Press, vol. 23, pp. 421-441.*

Ghosh, Amit, "Strain Localization in the Diffuse Neck in Sheet Metal", Jul. 1974, Metallurgical Transactions, vol. 5, pp. 1607.*

Prévost, J.H. and Hoeg, K, "Soil mechanics and plasticity analysis of strain softening", 1975, Géotechnique, No. 2, pp. 279-297.*

Cunat, Pierre-Jean, "Stainless steel properties for structural automotive applications", Jun. 2000, Paper presented at the Metal Bulletin International Automotive Materials Conference, Euro Inox, pp. 1-10.*

Wanatanbe, K., et al., "Simple prediction method for the edge fracture of steel sheet during vehicle collision (1$^{st}$ report)", 2006, LS-DYNA Anwenderforum, DYNAmore GmbH, pp. B-I-9 to B-I-14.*

Fernandes, J.V., Rodrigues, D.M., Menezes, L.F. and Vieira, M.F., A Modified Swift Law for Prestrained Materials, 1998, International Journ of Plasticity, vol. 14, No. 6, pp. 537-550.*

Rees, D.W.A., Sheet orientation and forming limits under diffuse necking, 1996, Applied Mathematical Modelling, vol. 20, issue 8, pp. 624-635.*

Huang, Pao C., "Fracture Criterion of Isotropic Materials", Sep. 1986, Naval Surface Warfare Center, NAVSWC TR 90-76, pp. 1-19.*

El-Magd, E., "Mechanical properties at high strain rates", Sep. 1994, Journal De Physique IV, Colloque C9, vol. 4, pp. C8-149 to C8-170.*

English language International Search Report for International Application No. PCT/JP2007/051711 filed Feb. 1, 2007.

Kengo Yoshida et al. "Stress-Based Forming Limit Criterion for Aluminum Alloy Tube". Journal of Japan Society for Technology of Plasticity, vol. 45 No. 517, pp. 123-128.

Yoshida, Kengo. "A evaluation method of formability for pre-strained steel sheet". CAMP-ISIJ, vol. 17. (with partial English language translation).

William F. Hosford et al. "Metal forming Mechanics and metallurgy". Prentice-Hall Inc., Englewood Cliffs, New Jersey. 1983. pp. 312-322.

Moriaki Goya et al. "An Expression of Elastic-Plastic Constitutive Law Incorporating a Stress Increment Dependence (1$^{st}$ Report, Initial Isotropic Materials with Mises Type-Plastic Potential)". The Japan Society of Mechanical Engineers. No. 87-1441B, pp. 1617-1622.

Toshihiko Kuwabara et al. "Constitutive modeling of aluminum alloys and its effect on forming simulations". Journal of Japan Institute of Light Metals, vol. 55, No. 8 (2005), pp. 363-370 (with partial English language translation).

Goldstein, P. V. et al., "Fracture Mechanics Fracture of Materials", Mechanics, News in the Foreign Science, MIR Publisher, Moscow, 1979, pp. 22-28.

RU Office Action issued Sep. 14, 2009 for Russian patent application No. 2008135325/28.

English-language translation of the International Preliminary Report on Patentability for International Application No. PCT/JP2007/051711 filed Feb. 1, 2007.

English-langauge translation of the Written Opinion of the International Searching Authority for International Application No. PCT/JP2007/051711 filed Feb. 1, 2007.

* cited by examiner

ISOTROPIC HARDENING

FRACTURE PREDICTION DEVICE

FRACTURE LIMIT OBTAINING DEVICE

FRACTURE LIMIT OBTAINING DEVICE

FRACTURE LIMIT OBTAINING DEVICE

FRACTURE PREDICTION METHOD, DEVICE, A PROGRAM ARRANGEMENT AND COMPUTER-ACCESSIBLE MEDIUM THEREFOR

CROSS REFERENCE TO RELATED APPLICATION(S)

The present application is a national phase application of International Application PCT/JP2007/51711 filed on Feb. 1, 2007 and published as International Publication WO 2007/088935 on Aug. 9, 2007. This application claims priority from the International Application pursuant to 35 U.S.C. § 365. The present application also claims priority from Japanese Patent Application Nos. 2006-024975 and 2006-24976, both filed on Feb. 1, 2006, under 35 U.S.C. §119. The disclosures of these applications are incorporated herein in their entireties.

FIELD OF THE INVENTION

The present invention relates to a fracture prediction method, a device, a program product and a recording medium for providing a thin plate formed of a metal material, and is particular, e.g., utilizing a fracture determining criterion for a material fracture in a crash process of an automobile member subjected to press-forming.

BACKGROUND INFORMATION

A margin against a fracture is determined in general using a thinning criterion or a forming limit diagram (FLD). The FLD indicates the major and minor strain ($\epsilon_1$ and $\epsilon_2$, respectively) at which the failure generally occurs, and can be used in a crash analysis. The FLD can be experimentally determined by loading specimens along various proportional paths. Nakazima et al., for example, describes an operation of hemispherical punch stretching for rectangular specimens with various widths. Before the forming operation, small circulars or grids are marked on the sheet surface by etching or printing. Theses circles are generally distorted into ellipses during the forming operation, which will be terminated at the onset of necking or crack. The size of an ellipse near the neck likely varies with the width of the specimen. The major and minor strains can be measured from the ellipse at the neck or crack. Finally, the forming limit curve (FLC) is drawn so that it fits the measured limit strains for various paths.

FIG. 1 shows an exemplary fracture limit curve measured by experiment. As an FLD prediction method, there may be a combined usage of Hill's criterion and Swift's one, Marciniak-Kuczynski model, Storen-Rice model, etc., and the FLD can be obtained by correcting the influence of a sheet thickness by a Keeler's empirical rule. The tearing can be produced by a dynamic FE code, whereas the former may not be detected in the FE analyses. Instead of direct predictions of the tearing, the computed strains are likely compared with critical values external prepared and it is regarded that the failure occurs when one of the computed strains reaches the limit. Certain additional documents which may be relevant to the technology described herein include CAMP-ISIJ17, 1063, 2004; and Metal Forming, Hosford, 319, 1993.

SUMMARY OF EXEMPLARY EMBODIMENTS OF THE INVENTION

FIG. 2 shows exemplary schematic illustration of experimental forming limit strains for (a) proportional loading, (b) uniaxial tension followed by equi-biaxial stretching, (c) equi-biaxial stretching followed by plane-strain stretching, and (d) equi-biaxial stretching followed by uniaxial tension. As provided in FIG. 2, the maximum curve can be observed in uniaxial tension followed by equi-biaxial stretching, whereas the minimum one is obtained for the opposite sequence. The FLC for equi-biaxial stretching followed by plane-strain stretching can be slightly higher than the minimum ones.

For example, in a car crash deformation process of an automobile body part subjected to press-forming or pre-deformation in press-forming, the strain path can often change. When evaluating a fracture using the forming limit strains obtained by experiment, forming limits strains must be prepared according to the an infinite number of strain paths. Therefore, in practice, the exemplary forming limit strain with respect to a proportional loading path may be used for evaluation of a fracture, and hence high prediction accuracy may not be expected.

Further, a steel sheets failure can occur under stretch-flanging when a stretch strain in the circumferential direction of a cutting edge reaches the critical value. The stress state in the cutting edge portion may be close to the uniaxial tension, but abrupt gradients of stress and strain exist inward from the cutting edge portion. Thus, the fracture limit can indicate a value that may be different compared to the fracture limit strain or stress obtained by a uniaxial tensile test. For example, high-strength steels over about 590 MPa can suffer from the breakage under stretch-flanging, even when the cutting edge portion reaches a plastic instability and localized necking (e.g., thickness necking) occurs, the inside material excluding the cutting edge portion may not be satisfied the plastic instability yet. Thus, being restrained by the inside material, the plastic instability cannot be reached as the whole, and progress of the localized necking may be delayed.

Furthermore, in the stretch-flanging limit, a large number of thickness necks are formed in a circumferential direction of the cutting edge portion, and thus the fracture is delayed. For example, assuming that a localized necking is formed at one position in the cutting edge portion, stress in the circumferential direction in the vicinity of the localized necking is eased. However, the influence of this ease of stress generally decreases with distance from the localized necking, and when the deformation proceeds further, a next localized necking is formed at a separated location from the first localized necking. When the deformation proceeds still further, a new neck is formed. Repeating this process, a large number of thickness necks are formed in the circumferential direction of the cutting edge portion, and the localized necking grow. Here, reason why the previously formed sheet thickness necks grow but do not lead to a fracture is that they are restrained by a material having a small strain, and does not satisfy the plastic unstableness as the entire cutting edge portion in the circumferential direction. Therefore, in the stretch-flanging limit, when a thickness neck is formed at one position in the circumferential direction of the cutting edge portion, it does not lead to a fracture but is delayed.

Thus, an exemplary prediction method for the stretch-flanging limit may not be simple due to an existence of the strain gradient inward from the cutting edge portion, and to a delay effect such that a fracture does not occur even when one position in the circumferential direction satisfies the localized necking. Thus, such exemplary method may be difficult to utilize and/or implement.

Exemplary embodiments of the present invention may be directed to solving the above-described problems of conventional arts as technical problems. For example, an exemplary object of the exemplary embodiments of the present invention can provide a fracture prediction method by which, when predicting presence of fracture occurrence in a steel sheet in a process including one or more strain paths, the fracture limit curve can be obtained easily and efficiently and presence of fracture occurrence can be predicted with high prediction accuracy. Further, the risk of fracture upon press forming or crashworthiness can be evaluated quantitatively, thereby realizing efficient and highly precise development of autobodies optimizing the material, the forming, and the car body structures for crash safety.

An exemplary embodiment of the fracture prediction method of the present invention can include a method for evaluating a fracture limit of a thin plate constituted of a metal material. Such exemplary method may include, when predicting fracture occurrence in the thin plate in a plastic deformation process according to one or more deformation path changes, a procedure of converting a fracture limit curve in strain space into a fracture limit curve in stress space, and a procedure of predicting presence of the fracture occurrence using the obtained fracture limit curve in stress space.

Further, e.g., a prediction with high accuracy may be possible by using a hole expansion ratio having a good correlation with a stretch-flanging limit as a criterion for a fracture, and further by performing fracture determination in stress space in which the influence of a deformation history can be considered, instead of strain space.

In addition, e.g., an exemplary embodiment of the fracture limit obtaining method of the present invention can include a method of obtaining a fracture limit used for determining a fracture limit of a thin plate constituted of a metal material, in which a stretch strain ratio λ obtained from a hole expansion test is converted into a fracture limit curve in stress space when determining a fracture limit of the thin plate in a process including one or more deformation path variations.

The exemplary fracture limit curve expressed in stress space may not depend on a deformation path, and hence can be expressed by a single limit curve. Therefore, using this as a fracture determining criterion, a fracture in a stretch flange portion including one or more deformation path variations can be determined with high accuracy.

According to the present invention, when predicting presence of fracture occurrence in a thin plate in a process including one or more deformation path variations, it is possible to obtain the fracture limit curve easily and efficiently and predict the presence of fracture occurrence with high prediction accuracy. Thus, the risk of fracture upon press forming or crash can be evaluated quantitatively, thereby realizing efficient and highly precise development of an automobile body considering the material, the construction method, and the structure at the same or similar time.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figure showing illustrative embodiment(s), result(s) and/or feature(s) of the exemplary embodiment(s) of the present invention, in which.

Figure 1:
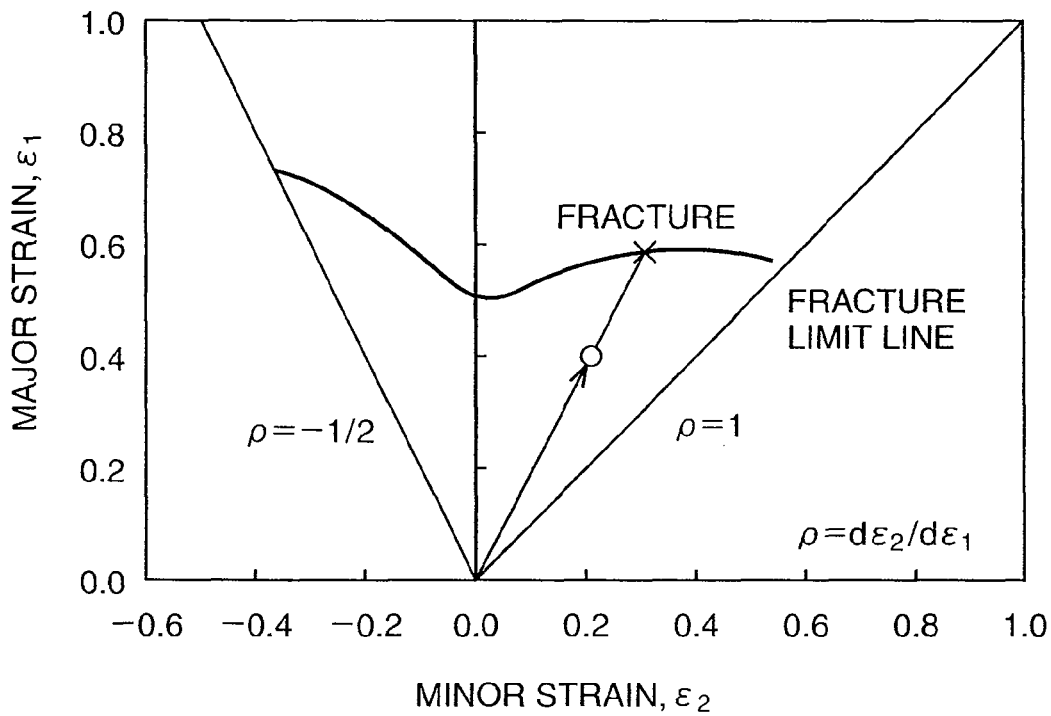
FIG. 1 is a graph showing a forming limit diagram (FLD) used for explaining a conventional knowledge.
Figure 2:
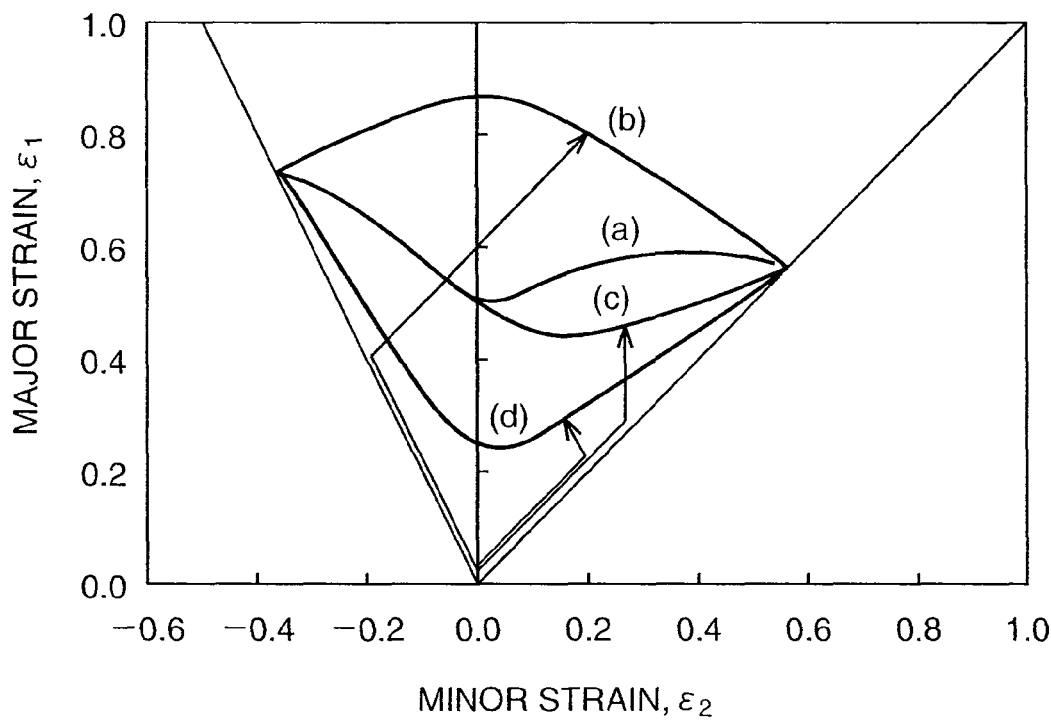
FIG. 2 is a forming limit graph used for explaining exemplary problems to be solved by exemplary embodiments of the present invention.

Throughout the figures, the same reference numerals and characters, unless otherwise stated, are used to denote like features, elements, components or portions of the illustrated embodiments. Moreover, while the present invention will now be described in detail with reference to the figures, it is done so in connection with the illustrative embodiments.

DETAILED DESCRIPTION OF EXEMPLARY EMBODIMENTS

First Exemplary Embodiment

A margin against a fracture when evaluating formability is determined in general using a thinning criterion or an FLD, which can be used for fracture prediction in a car crash analysis as well. Among them, the FLD is known to vary largely depending on a strain path changes, and cannot be expected to have high prediction accuracy as a method of evaluating a fracture in a plastic deformation process, in which the deformation path varies largely as in crash of an automobile body part subjected to press-forming or pre-deformation in press-forming.

However, recently Kuwabara et al. (e.g., described in Journal of the Japan Society for Technology of Plasticity, 45, 123, 2004; and Non-patent Document 2: CAMP-ISIJ 17, 1063, 2004) verified by experiment and analysis that, using a fracture limit curve expressed in stress space with an aluminum extruded material or mild steel sheets being the subject, the fracture limit can be represented almost uniquely without depending on the path of deformation. This knowledge relates to aluminum or mild steel sheets and is not clarified for high strength steels over 440 MPa, and hence cannot be used for current development of an automobile body in which high-strength steel sheets are mainly used.

Accordingly, the exemplary embodiment of the present invention can be achieved as follows:

(1) When a detailed experiment is performed on high-strength steel sheets having tensile strength of 440 MPa or higher and a fracture limit curve expressed in stress space is used, the fracture limit can be expressed by a single fracture limit curve without depending on the deformation path. (2) By using the fracture limit curve expressed in stress space, it is possible to predict a fracture evaluation in a plastic deformation process with high accuracy, in which the deformation path varies largely as in crash of an automobile body part subjected to press-forming or pre-deformation in press-forming.

EXAMPLES

Hereinafter, a first exemplary embodiment is explained in detail based on various examples.

Example 1

First, an exemplary method for obtaining the fracture limit curve in stress space will be explained. With a steel sheet shown in Table 1 below being the subject, there were measured (1) a fracture limit strain on a proportional loading path, and (2) a fracture limit strain under a deformation path variation. Here, t represents the thickness of a thin plate, YP represents proof strength, TS represents ultimate tensile strength, U.El represents uniform elongation, El represents total elongation, $r_m$ represents average r value (indicating a Lankford value and is expressed by $r_m=(r_0+2r_{45}+r_{90})/4$ where r value in the rolling direction is $r_0$, r value in the 45° direction with respect to the rolling direction is r45, and r value in the 90° direction with respect to the rolling direction is r90), and K, $\epsilon_0$, n represent material parameters obtained when a stress-strain curve obtained from a uniaxial tensile test is fitted in a function expression $$\sigma_{eq}=K(\epsilon_{eq}+\epsilon_0)^n. \qquad \text{[Equation 1]}$$

For the fracture limit strain on a proportional loading path, a fracture strain was measured with a scribed circle diameter being 6 mm by a uniaxial tension, a Nakajima method (hemispherical punch stretching using a Teflon (registered trademark) sheet), and a hydraulic bulge test. On the other hand, for the fracture limit curve under strain path changes, after a tension of 10% along the rolling direction is performed as first deformation, a fracture strain was measured by the uniaxial tension and the Nakajima method so that the direction of 90° degrees from the primary extension direction is the maximum principal stress.

TABLE 1

MECHANICAL PROPERTY VALUES OF MATERIAL AND MATERIAL PARAMETERS

| t/mm | YP | Ts | U. El | El | $r_m$ | K | $\epsilon_0$ | n |
|------|-----|-----|-------|----|-------|-----|--------|-------|
| 1.2 | 460 | 598 | 12 | 23 | 1.00 | 937 | 0.0108 | 0.157 |

(UNIT t: mm; YP, TS, K: MPa; El, U. El: %)

Conversion from a strain to a stress becomes possible by assuming (1) incompressibility, (2) Mises' yield function, (3) material hardening law with isotropy, (4) normality rule, and (5) membrane state of stress. Hereinafter, a specific method for converting the fracture limit curve in strain space into stress space will be explained.

The FLD of strain space is a diagram showing a major strain $\epsilon_{11}$ giving the fracture limit for each minor strain $\epsilon_{22}$, and a thickness strain $\epsilon_{33}$ can be obtained by them and the constant volume law $$(\epsilon_{33} = -(\epsilon_{11} + \epsilon_{22}))$$ [Equation 2]

Normally, as the constitutive law used in a forming analysis or crash analysis, there is used the isotropic hardening law assuming that an equivalent plastic stress $\sigma_{eq}$ is the unique function of an equivalent plastic strain $\epsilon_{eq}$ regardless of the path of deformation, and can be represented using a Swift's work-hardening law as $$\sigma_{eq} = K(\epsilon_{eq} + \epsilon_0)^n$$ [Equation 3]

As the function of work hardening, for example, the high-degree polynomial expression of an equivalent plastic strain or another form may be used, but it is preferable to use the Swift's equation, which is highly precise in approximation and is used frequently in a numerical simulation of a thin steel sheet.

Using the Mises' yield function for a yield surface for example, the equivalent plastic strain $\epsilon_{eq}$ can be represented as

[Equation 4]

$$\varepsilon_{eq} = \int d\varepsilon_{eq} \int \sqrt{\frac{2}{3} d\varepsilon_{ij} d\varepsilon_{ij}},$$

and can be obtained using a Hill's anisotropic criterion in the case of planar isotropy by

[Equation 5]

$$\varepsilon_{eq} = \int \frac{1+r}{\sqrt{2r+1}} \sqrt{d\varepsilon_{11}^2 + d\varepsilon_{22}^2 + \frac{2r}{1+r} d\varepsilon_{11} d\varepsilon_{22} + \frac{2}{1+r} d\varepsilon_{12}^2}$$

When using the Hill's anisotropic yield function, the plastic anisotropic parameter r value is required, which can be obtained specifically by $r_0 = (r_0 + 2r_{45} + r_{90})/4$ from r values ($r_0$, $r_{45}$, $r_{90}$) in the directions of 0°, 45°, 90° from the rolling direction.

In addition, a high-degree anisotropic yield function may be used as necessary, but it has many parameters and requires considering the direction in a plate surface while processing, and hence provides insufficient improvement in precision even though it is complicated. Thus, in practice, the yield function assuming planar isotropy is sufficient. In either yield function, the equivalent plastic stress $\sigma_{eq}$ considering a deformation path variation can be obtained using the equivalent plastic strain $\epsilon_{eq}$ obtained by integrating an equivalent plastic strain increment $d\epsilon_{eq}$ on a strain path and the work-hardening law.

Figure 3:
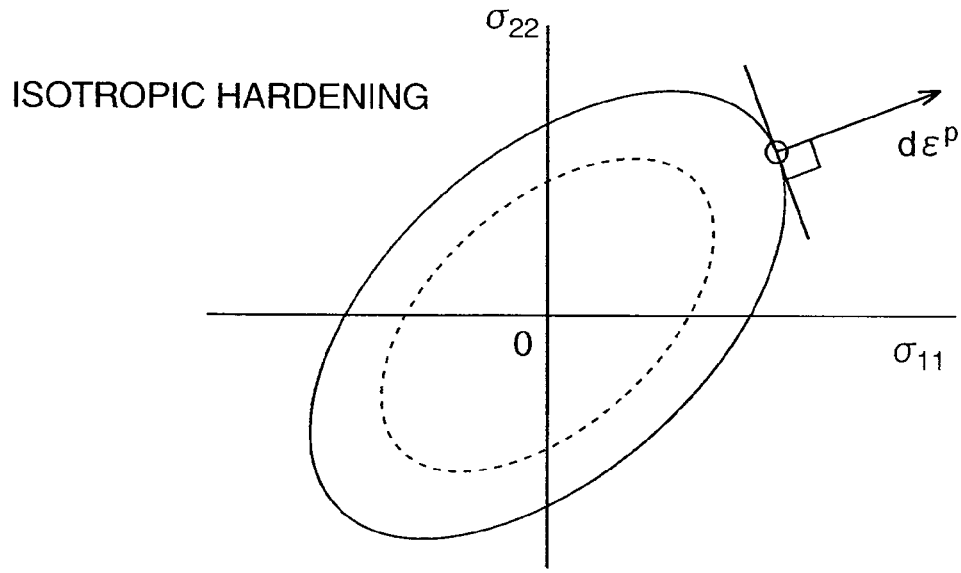
FIG. 3 is a diagram for explaining a conversion from a strain into a stress.

Next, a deviation stress component $\sigma_{ij}$ is obtained by isotropic hardening of yield surface shown in FIG. 3 and the normality rule

[Equation 6]

$$\sigma'_{ij} = \sigma_{eq} \frac{\partial \varepsilon_{eq}}{\partial \varepsilon_{ij}}$$

Further, by assuming the plane stress ($\sigma_{33} = 0$), the stress component $\sigma_{ij}'$ can be obtained from $$\sigma_{ij} = \sigma_{ij}' - \sigma_{33}' \delta_{ij}$$ [Equation 7]

Figure 4:
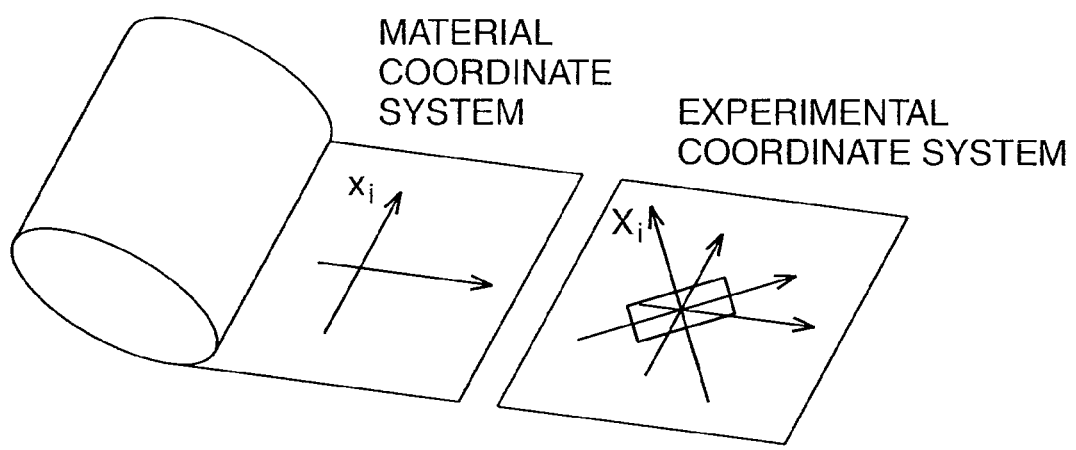
FIG. 4 is a diagram for explaining a coordinate transformation law.

When the main axis of the strain and the rolling direction do not match as shown in FIG. 4, a coordinate transformation operation shown below is preferable. In the diagram, $x_i$ represents $x_1$ axis//RD, $x_2$ axis//TD, $x_3$ axis//ND which coordinate axes of a material coordinate system, and $X_i$ represents the main axis of the strain in an n-th order deformation. When a component display on the material coordinate system of a tensor A is $\hat{A}_{ij}$, and a coordinate converted tensor is R, (1) a strain component $\epsilon_{ij}$ measured by an experimental coordinate system can be converted into a strain component $$\hat{\epsilon}_{ij} = R_{pi} \epsilon_{pq} R_{qj}$$ [Equation 8]

with the material coordinate system being the reference coordinate by a coordinate transformation law. Next, a deviation stress component $\hat{\sigma}_{ij}'$ is obtained from (2) the yield function modeled with the material coordinate system being the reference coordinate system and the normality rule, and finally (3) the coordinate transformation law is used to obtain a stress component $$\sigma_{ij}' = R_{ip} \hat{\sigma}_{pq}' R_{jq}$$ [Equation 9]

with the experimental coordinate system being the reference coordinate.

Figure 5:
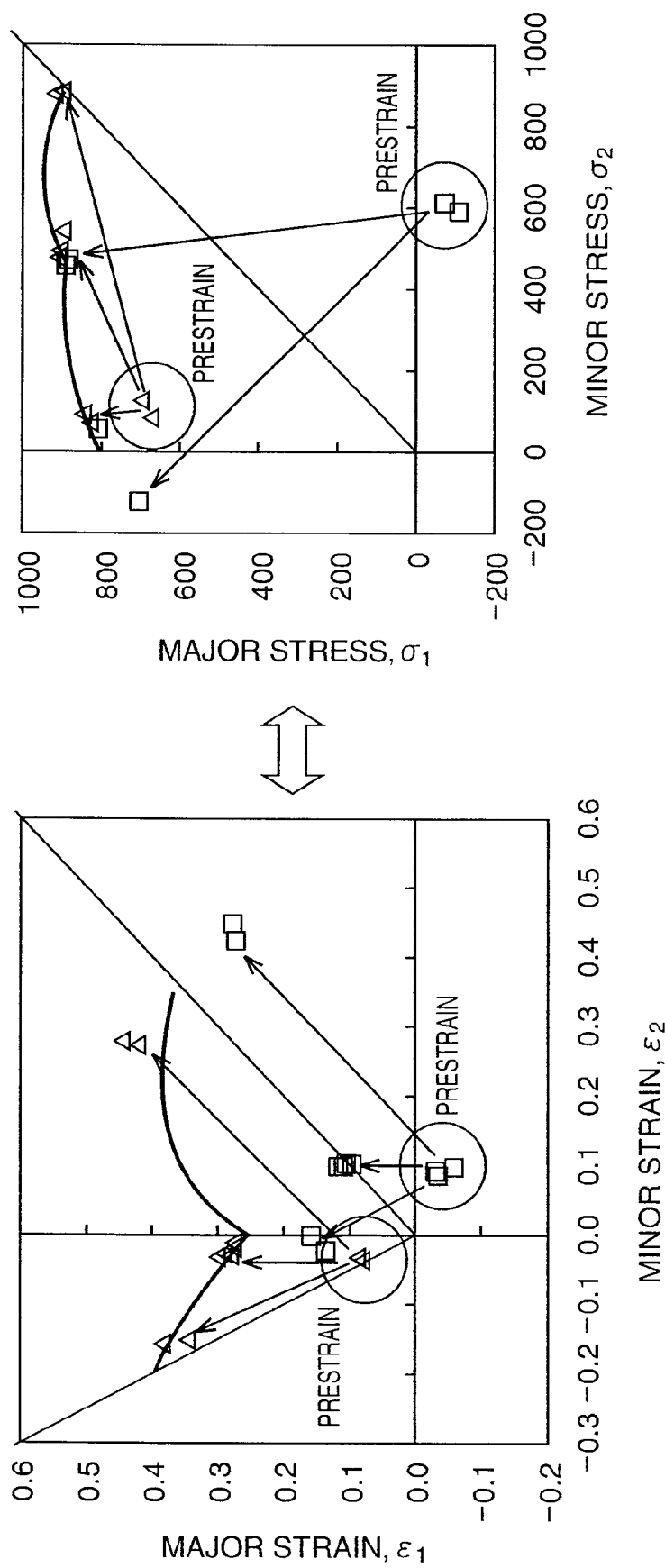
FIG. 5 are graphs showing that, while an FLD of strain space depends on a strain path and a fracture limit curve thereof varies largely, a fracture limit curve in stress space can be expressed by a single curve.

FIG. 5 shows a graph of an exemplary FLD measured by experiment, and an exemplary fracture limit curve obtained by converting the FLD into stress space with a major stress and a minor stress by the aforementioned method. The FLD of strain space depends on the deformation path and the fracture limit curve varies largely, but the fracture limit curve expressed in stress space becomes a single fracture limit curve.

Further, as a result of performing experiments and studies on high-strength steel sheets of 440 MPa to 980 MPa classes shown in Table 2 below, regardless of the tensile strength of a material or strengthening mechanism, single fracture limit curves can be produced in a wide range. Using these exemplary fracture limit curves expressed in stress space, fracture evaluation in a plastic deformation process in which the deformation path varies largely, as in a car crash of an automobile body part subjected to press-forming or pre-deformation in press-forming, can be predicted with high accuracy.

A fracture limit curve obtained by converting an FLD measured by an experimental method other than the Nakajima method into stress space may be used, or a fracture limit curve obtained by converting a theoretical FLD of Hill's localized necking model, Swift's diffuse necking model, Marciniak-Kuczynski method, Storen-Rice model, or the like into stress space may be used for the fracture prediction.

TABLE 2

MECHANICAL PROPERTY VALUES OF MATERIAL AND MATERIAL PARAMETERS

| MATERIAL | t | YP | TS | U. El | El |
|---|---|---|---|---|---|
| A: 440 MPa SOLID SOLUTION-HARDENED STEEL | 1.2 | 368 | 460 | 18 | 35 |
| B: 590 MPa PRECIPITATION-HARDENED STEEL | 1.2 | 460 | 598 | 12 | 23 |
| C: 780 MPa DUAL-PHASE STEEL | 2.0 | 490 | 840 | 10 | 19 |
| D: 980 MPa DUAL-PHASE STEEL | 2.0 | 710 | 1010 | 8 | 14 |

(UNIT t: mm; YP, TS: MPa; El, U. El: %)

Further, an exemplary method of evaluating a fracture limit is described. For predicting fracture of a material by a numerical simulation by a finite element method (FEM), there may be the following technical problems:

(1) An FLD measured by experiment is affected strongly by a distance between evaluation points and a friction state. Thus, when using the FLD as a fracture determining criterion, correction according to analysis conditions of the numerical simulation is necessary.

(2) In the numerical simulation, increase of strain up to a uniform deformation can be simulated precisely, but for simulating localized necking occurring in a region to the extent of a sheet thickness or a shear band in which the strain is localized in a narrower region, finite elements have to be segmented adequately. Thus, the prediction is difficult with the performance of current computers.

(3) With the material constitutive law adopted normally in general purpose software, localization of a strain is delayed, and hence evaluation on the risk side is given when the actually measured FLD is taken as the fracture determining criterion.

An exemplary embodiment of the present invention provides a clarification of a fracture determining criterion suitable for numerical simulations. With the steel sheets shown in Table 1 being taken as subjects, the FEM numerical simulation of hemispherical punch stretching is performed, and influences of an element size and a material constitutive equation on the localization process of a strain are examined.

Figure 6:
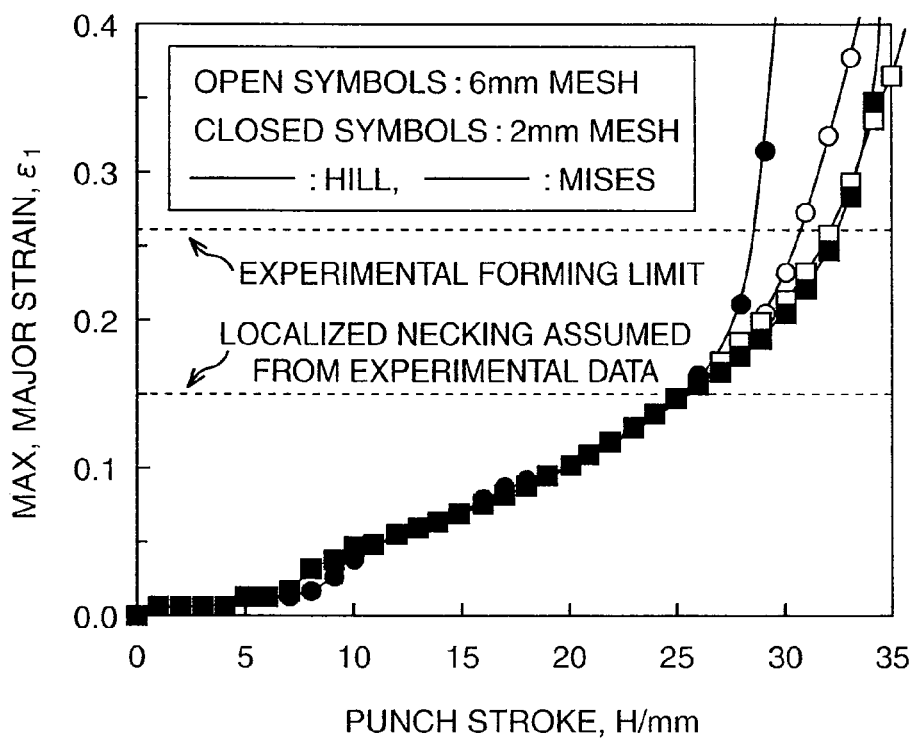
FIG. 6 is a graph showing a relationship between a punch stroke and maximum major strain.

FIG. 6 shows a graph of a relationship of a maximum major strain introduced by punch-stroke and press-forming. The influences of the element size and the material constitutive equation barely appear from the beginning of the formation to the punch-stroke of approximately 25 mm, but these influences become obvious beyond 25 mm where localization of the strain begins.

Figure 7:
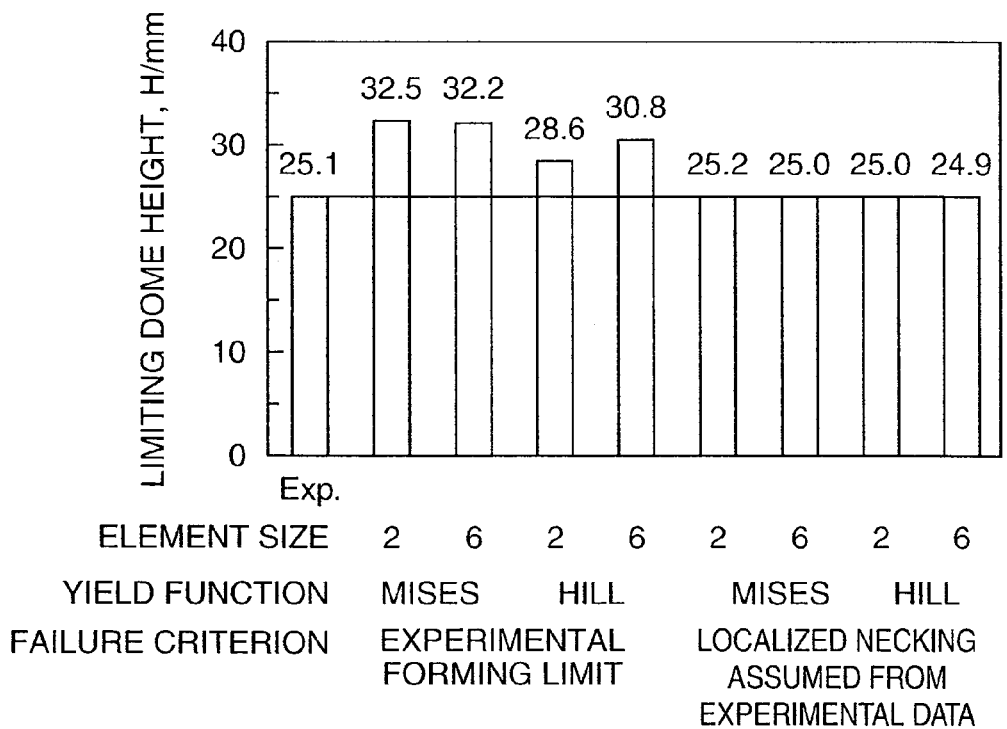
FIG. 7 is a graph showing a comparison of a prediction accuracy when performing a numerical simulation with various analysis conditions and using an FLD obtained by experiment and a localized necking occurrence limit as a fracture determining criterion.

FIG. 7 shows a graph of a comparison of prediction accuracy when performing the numerical simulation with various analysis conditions and using an FLD obtained by experiment and a localized necking occurrence limit as a fracture determining criterion. When the actually measured FLD is used as the fracture determining criterion, the localization process of a strain cannot be simulated precisely, and thus the accuracy of fracture prediction is not high. On the other hand, when the localized necking occurrence limit is used as the fracture limit, prediction with relatively high accuracy becomes possible regardless of the element size and the used material constitutive equation, and evaluation on the safe side can be obtained. This can suggest that the localized necking occurrence limit may be used as the fracture determining criterion in practice because a ductile fracture in a steel sheet occurs at a position where deformation is localized by localized necking, and when localized necking occurs it leads to a fracture by very short time.

The localized necking occurrence limit can be handled within the framework of plastic instability, and can be predicted by a theoretical FLD of Hill's localized necking model, Swift's diffuse necking model, Marciniak-Kuczynski method, Storen-Rice model, etc.

As shown in this example, as a result of dedicated studies, the present inventors have found that high prediction accuracy can be assured by using as the fracture determining criterion the fracture limit curve obtained by converting a necking start curve in strain space into stress space when evaluating a fracture by the numerical analysis simulation using the finite element method.

Figure 8:
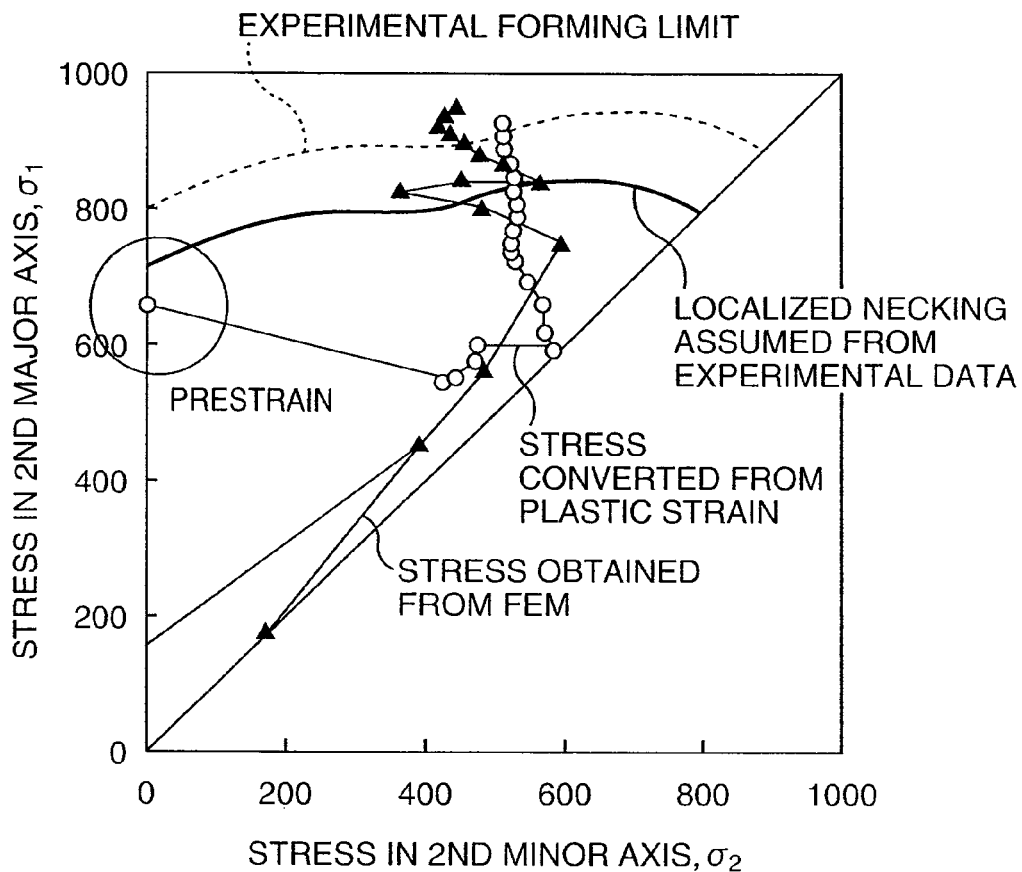
FIG. 8 is a graph showing a positional relationship between a stress history in a formation process obtained by a numerical simulation and a fracture limit curve.

Next, a case example of an exemplary method for evaluating a fracture limit is described. Such case example of fracture prediction is provided on a non-linear path such that with the steel sheets shown in Table 1 being the subjects, an uniaxial tension of 10% in the rolling direction is performed as first deformation, and thereafter plane strain deformation is performed by hemispherical punch stretching. FIG. 8 shows a graph of an exemplary relationship between a stress history in a formation process obtained by a numerical simulation and a fracture limit curve obtained by converting a necking start curve in strain space into stress space.

When using a dynamic explicit method for the numerical simulation, the exemplary obtained stress increases while vibrating largely because propagation of a stress wave is solved at minute time intervals without performing repetitive calculation within a time step. With this method of comparing a positional relationship between a stress and a fracture limit stress to evaluate a fracture, it may be difficult to assure a high prediction accuracy.

According to one exemplary embodiment of the present invention, a method of determining a fracture with high accuracy can be provided, which can avoid or reduce, when using the dynamic explicit method for the numerical simulation, vibration of a stress by converting a plastic strain into a stress by post-processing.

Figure 9:
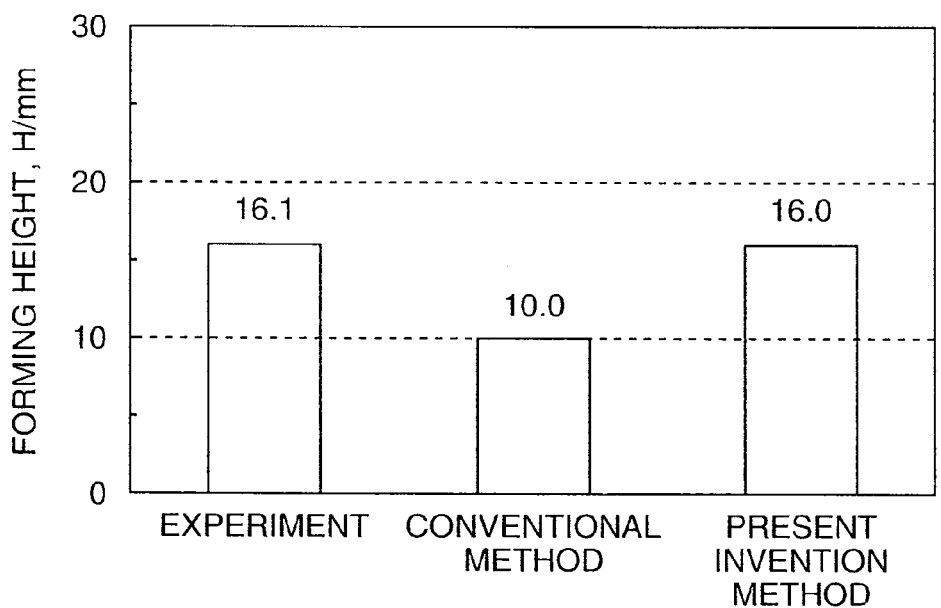
FIG. 9 is a graph showing prediction accuracy of exemplary embodiments of a method according to the present invention.

FIG. 9 shows a graph of exemplary results of predicting a fracture using the exemplary embodiment of a method according to the present invention. With a conventional fracture prediction method using, e.g., FLD, prediction with high accuracy is difficult since the fracture limit curve varies largely depending on a deformation path. In contrast, by applying the exemplary embodiment of the present invention, a fracture can be predicted with good accuracy even when the deformation path varies. In addition, the exemplary embodiment of the present invention can be used to evaluate a fracture by comparing a positional relationship between a value obtained by converting an experimental strain measurement result into a stress and a fracture limit curve, instead of performing the numerical simulation using the exemplary finite element method.

Figure 10:
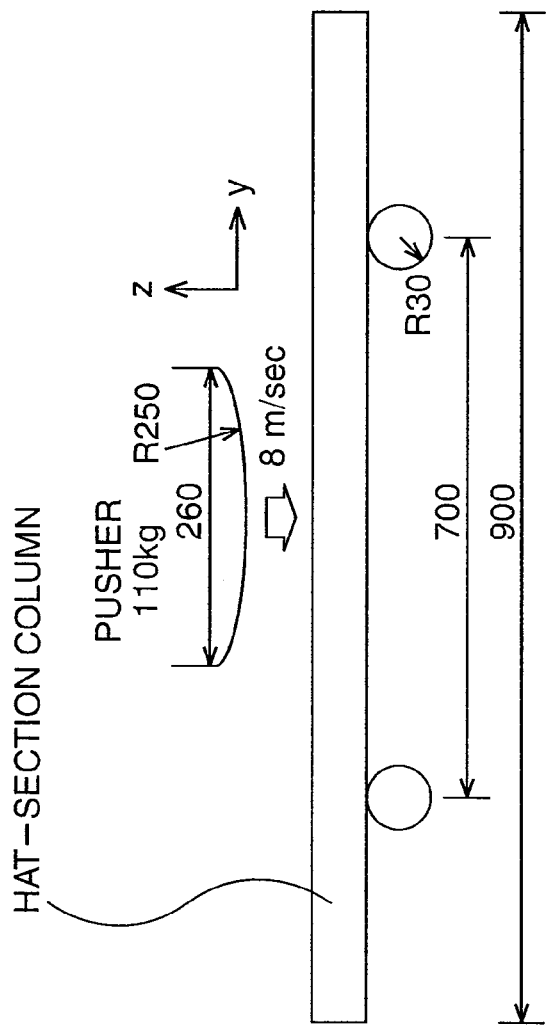
FIG. 10 is a diagram showing an exemplary embodiment of a part with a hat cross-sectional shape, which is a target of verifying prediction accuracy of a crash analysis and the overview of a three-point bending drop weight test.
Figure 10:
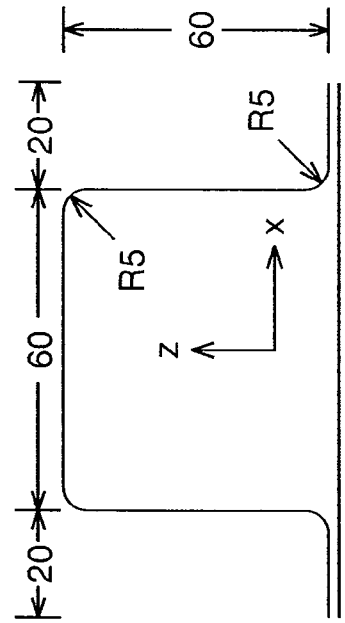

Next, an example of applying the exemplary fracture prediction method to a crash analysis is described. With the steel sheets shown in Table 1 being the subjects, the fracture prediction method of the present invention is applied in an exemplary embodiment of a three-point bending crash analysis of a member shown in FIG. 10 with a hat cross-section and a length of about 900 mm.

Figure 11:
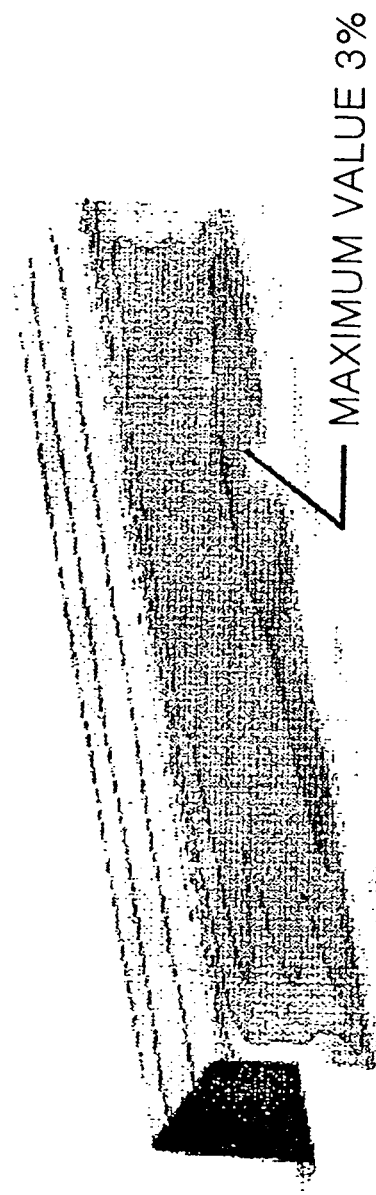
FIG. 11 is illustration of an analysis result of draw-bending formation of a hat shape by a numerical simulation.

First, an analysis of draw-bending in a hat shape was performed using the numerical simulation of the dynamic explicit code. The result of the exemplary forming simulation is shown in FIG. 11. Next, a finite element model for a crash analysis can be created, on which spot-welding processing with a flat plate (with a relative displacement between two contact points being fixed) at 30 mm intervals is performed at a flange portion.

Further, the obtained exemplary forming analysis result is reflected on this exemplary finite element model for a crash analysis, and the crash analysis may be performed by the numerical simulation by the dynamic explicit code. When evaluating a fracture in a material in a crash process after press-forming, the deformation history during formation can be considered by inheriting a thinning and an equivalent plastic strain obtained by the numerical simulation of press-forming, or a thinning and an equivalent plastic strain, a stress tensor, a strain tensor as initial conditions of the crash analysis.

The deformation history during formation can be considered by measuring a thickness of a press-formed product and an equivalent plastic strain by an experiment instead of the numerical simulation and inheriting one of them as an initial condition of the crash analysis.

In the case examples described herein above, the quasi-static plastic deformation process such as press-forming is handled, with a mechanical characterization likely at high strain rates needs to be considered in the car crash analysis. It is known that steels have strain rate dependency, and flow stress increases when the deformation speed is high. During an automobile crash, the strain rate may reach about 1000/s in a corner where deformation concentrates. For assuring prediction accuracy in the crash analysis, it may be preferable to consider accurate mechanical characterization at high strain rates.

Figure 12:
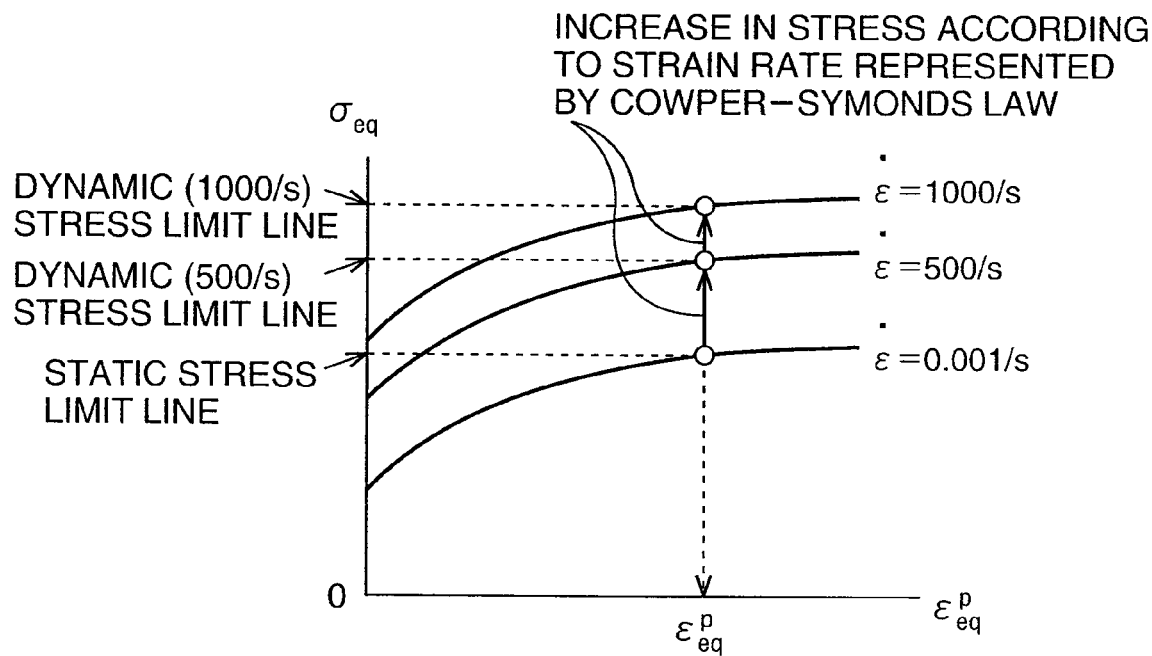
FIG. 12 is a graph showing a relationship between an equivalent plastic strain and an equivalent stress according to a strain speed.
Figure 13:
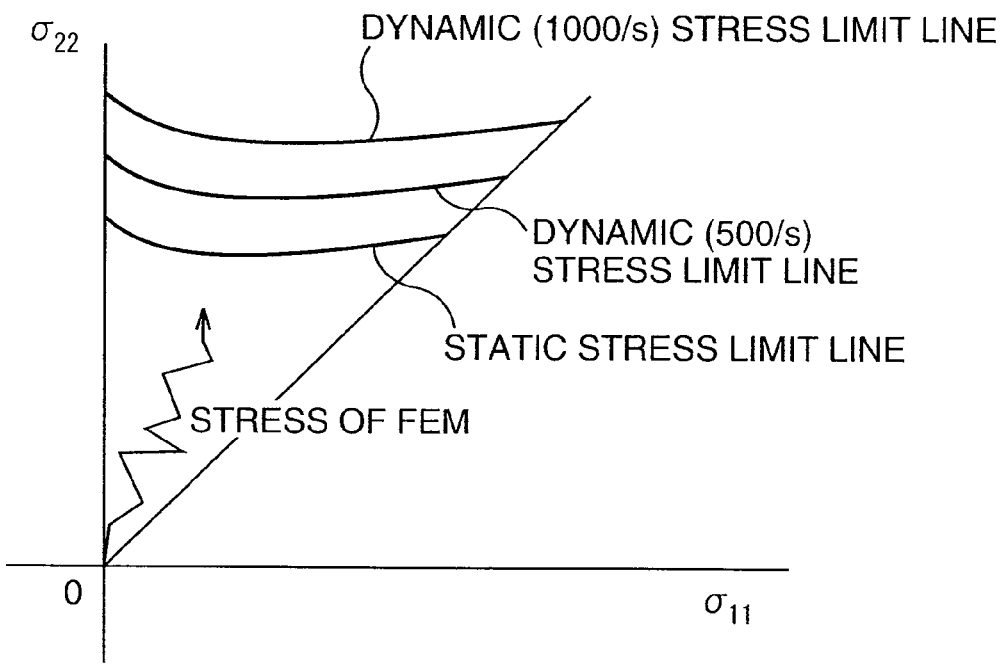
FIG. 13 is a graph showing a positional relationship between a dynamic fracture stress limit curve in stress space and a dynamic stress obtained from a crash simulation.

Generally, when performing the crash analysis with the numerical simulation by the exemplary finite element method, the Cowper-Symonds equation can be used as a material model representing increase of stress according to a strain rate. FIG. 12 shows a graph of an exemplary relationship between an equivalent plastic strain and an equivalent stress according to a strain rate. FIG. 13 shows a graph of an exemplary positional relationship between a dynamic fracture stress limit curve in stress space and a dynamic stress obtained from a crash simulation.

When evaluating a fracture using the dynamic stress obtained from the crash simulation, a large number of dynamic fracture stress limit curves are needed depending on the strain rate, and practically it is difficult to predict the fracture.

According to an exemplary embodiment of the present invention, the stress at a reference strain speed obtained by converting a plastic strain obtained from the crash simulation may be used, and only the fracture stress limit curve at the single reference strain rate may be used as the fracture limit (fracture criterion) used for fracture determination. Thus, the reference strain rate may be a quasi-static strain rate. Although the range of the quasi-static strain rate differs depending on the material, the fracture limit curve measured in the range of about 0.001/s to 1/s may be used in practice.

Figure 14:
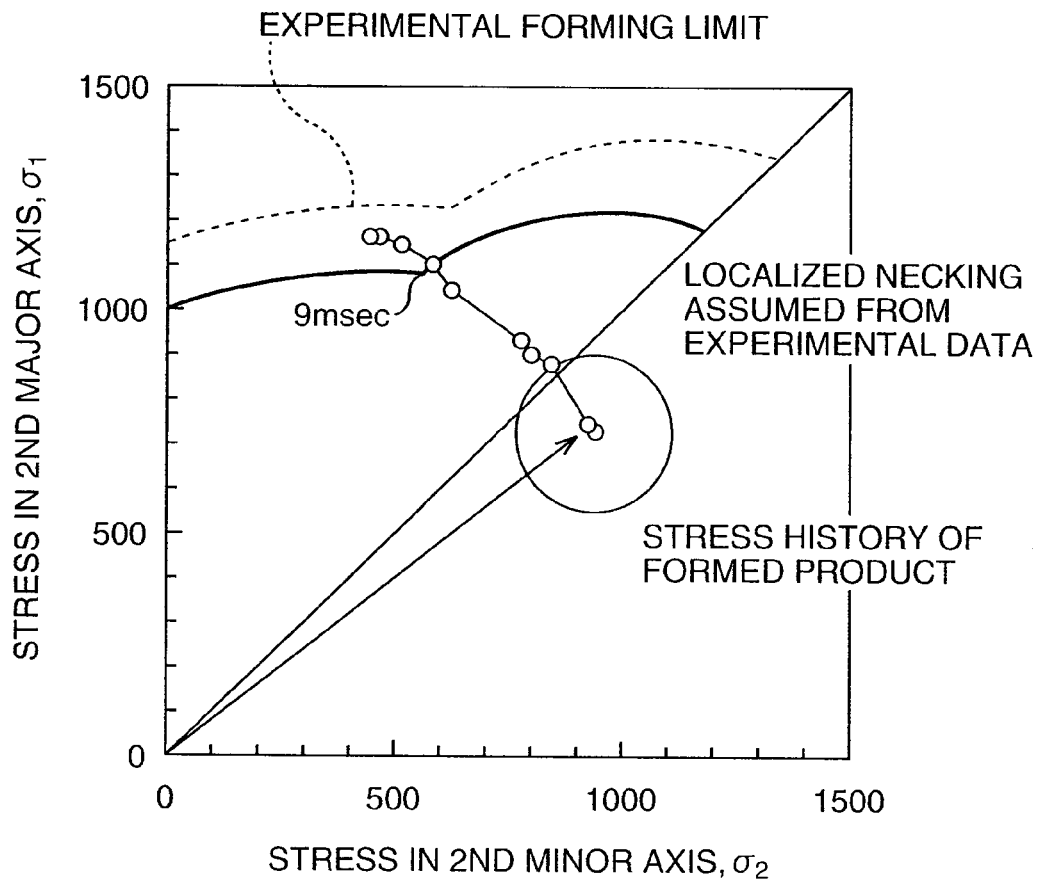
FIG. 14 are graphs showing a positional relationship between a stress history in a formation process obtained by a numerical simulation and a fracture limit curve, and prediction accuracy of exemplary embodiments of the method according to the present invention.
Figure 14:
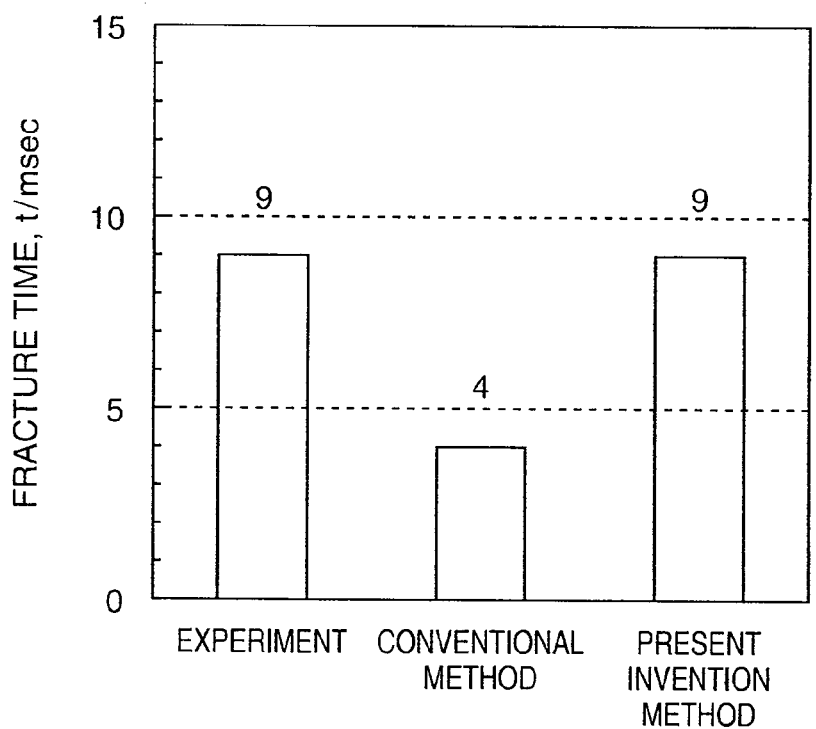

FIG. 14 shows a graph of an exemplary result of predicting a fracture with an exemplary embodiment of the method of the present invention. With a conventional fracture prediction method using FLD, it can be difficult to predict with high accuracy a plastic deformation process in which a deformation path varies largely as in a crash phenomenon after subjected to pre-deformation in press-forming. However, by applying the exemplary embodiment of the present invention, a fracture can be predicted with good accuracy even in a crash process after press-forming.

As shown in the above examples, according to the exemplary embodiment of the present invention, a risk of fracture can be evaluated quantitatively from data obtained by simulating press-forming and crash processes of a steel sheet by the exemplary embodiment of a finite element method. For example, the Cowper-Symonds equation is used as a representative example as the strain rate dependency of a deformation stress, but the effectiveness of the exemplary embodiment of the present invention may not change even using an arbitrary constitutive equation, for example an m-th power hardening equation, a Johnson-Cook equation, or the like, with which the strain rate dependency can be considered.

Example 2

Described below, as several specific examples of the exemplary embodiment of the present invention, an exemplary stretch-flanging limit evaluation method with a hole expansion ratio $\lambda$ in stress space being a criterion is described. As test specimens, sheets having 1.2 mm in thickness, of a cold-rolled and continuously annealed, dual phase steel, having the mechanical properties shown in Table 3 have been used. The mechanical properties are obtained using JIS-5 specimens cut out in the rolling direction of the steel sheets and a screw-driven tester at a cross-head velocity of about 10 mm/min (a strain rate of about $3 \times 10^{-3}$/s).

TABLE 3

| TENSILE PROPERTIES OF DUAL-PHASE STEEL SHEET | | | | | | | | |
| --- | --- | --- | --- | --- | --- | --- | --- | --- |
| t/ mm | YP/ MPa | TS/ MPa | U. El (%) | El (%) | K/ MPa | $\epsilon_0$ | n' | $r_m$ |
| 1.2 | 354 | 614 | 17 | 30 | 1109 | 0.0070 | 0.230 | 0.89 |

(YP: PROOF STRENGTH, TS: ULTIMATE TENSILE STRENGTH, U. El: UNIFORM ELONGATION, El: TOTAL ELONGATION, $r_m$: LANKFORD VALUE)

Figure 15:
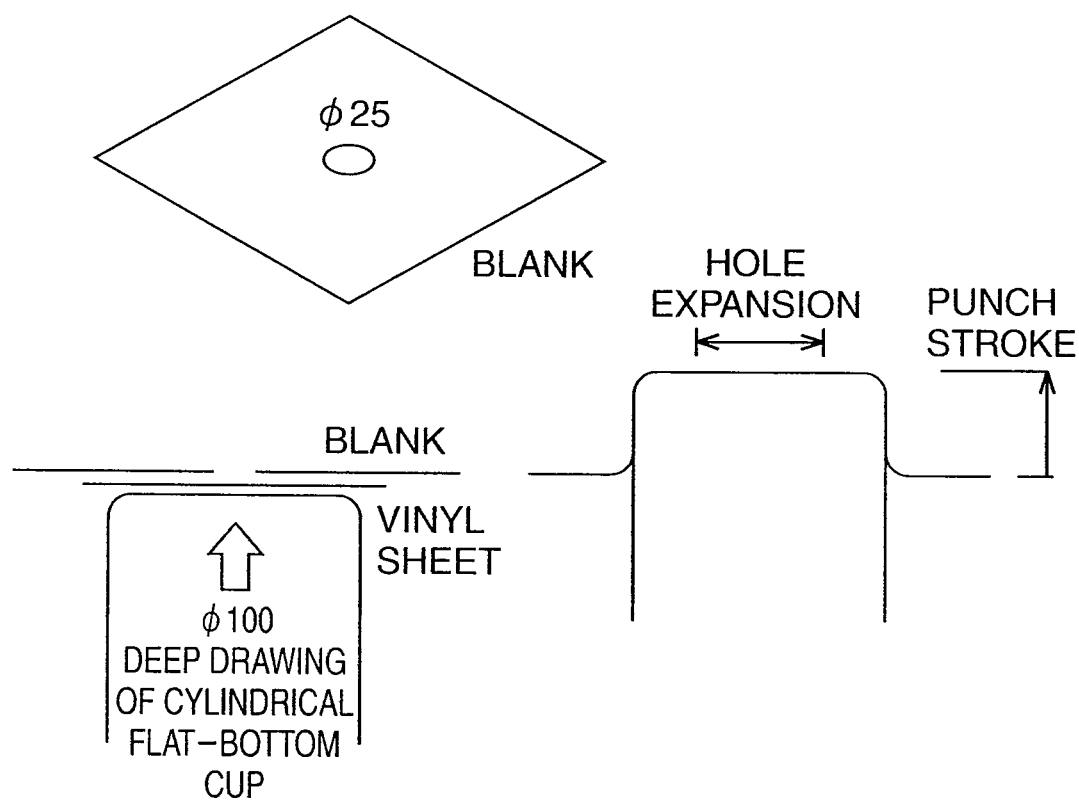
FIG. 15 is a diagram used for explaining an example of an exemplary embodiment of the present invention, and explaining an exemplary embodiment of an experiment method.

First, the steel sheet was sheared by the size of 200 mm×200 mm, and a hole with a diameter of 25 mm was punched through a center portion using a punch and a die. This steel sheet with a hole in the center was subjected to formation (Teflon sheet lubrication) with a flat-bottom punch with a diameter of 100 mm and a die shoulder R of 15 mm until a fracture occurs at a hole edge, and the hole diameter and the forming limit height when the fracture occurred were measured. The overview of the experiment is shown in a diagram of FIG. 15. Further, the FLD was measured by the Nakajima method (hemispherical punch stretching using a Teflon sheet) for use as the criterion for fracture prediction in the numerical simulation.

Figure 16:
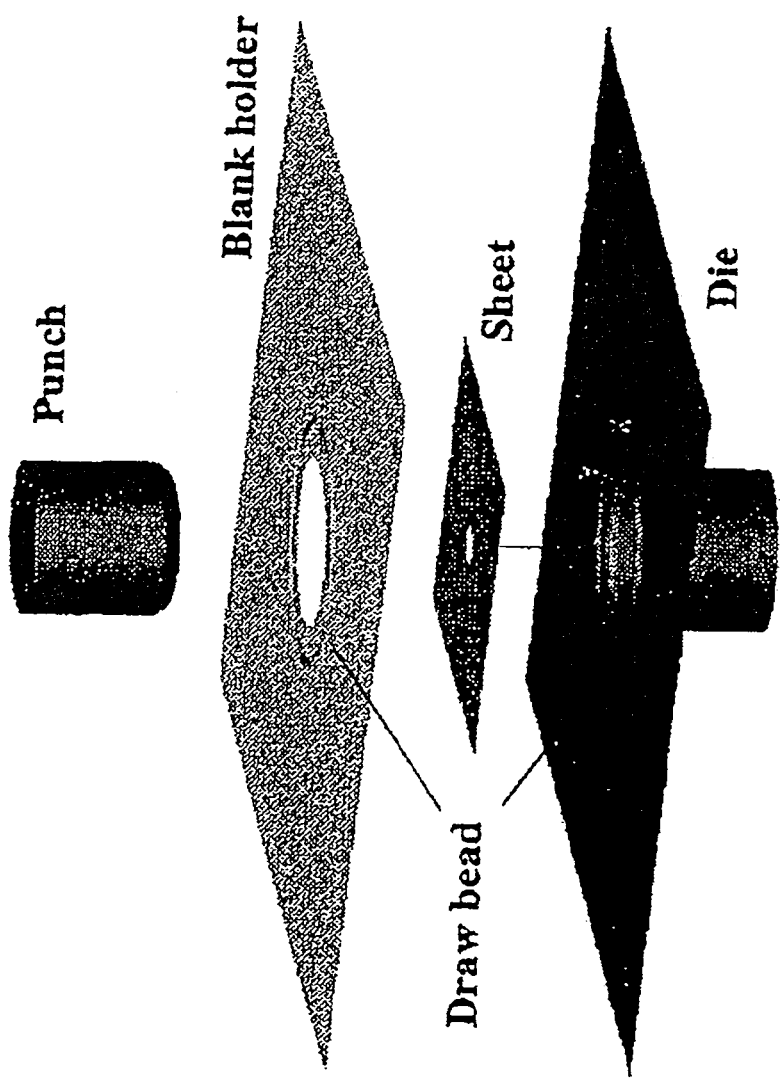
FIG. 16 is an illustration for explaining an exemplary embodiment of an example of the present invention, and explaining an exemplary embodiment of an analysis model.

Subsequently, the numerical simulation by the dynamic explicit FE code was performed to verify the prediction accuracy of a stretch-flanging limit that fractures from cutting edge. Note that the material parameters provided for the numerical simulation are the ones used for the experiment, and the tools comply with those of the experiment. An analysis model is shown in FIG. 16. The element size of 2 mm is used, which is equal to the distance between evaluation points when measuring the FLD, and a Hill's anisotropic yield function is used as the yield function for consideration.

Figure 17:
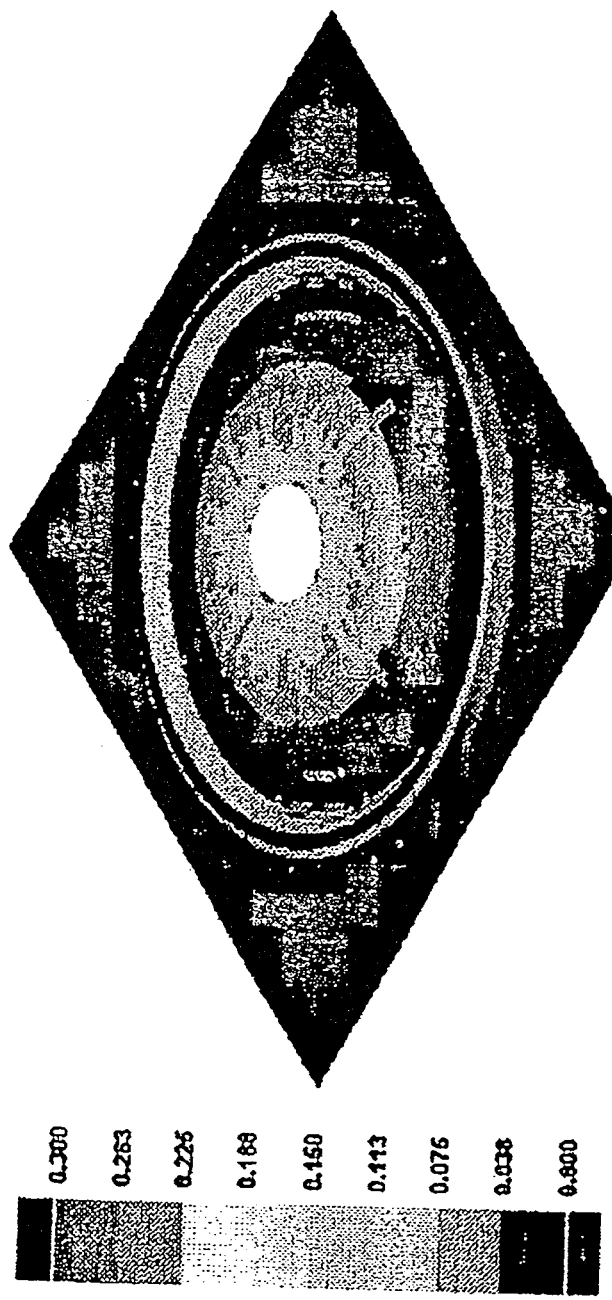
FIG. 17 is an illustration for explaining an exemplary embodiment of an example of the present invention, and a contour displaying an exemplary analysis result with respect to a major strain distribution; an exemplary embodiment of an example of the present invention
Figure 18:
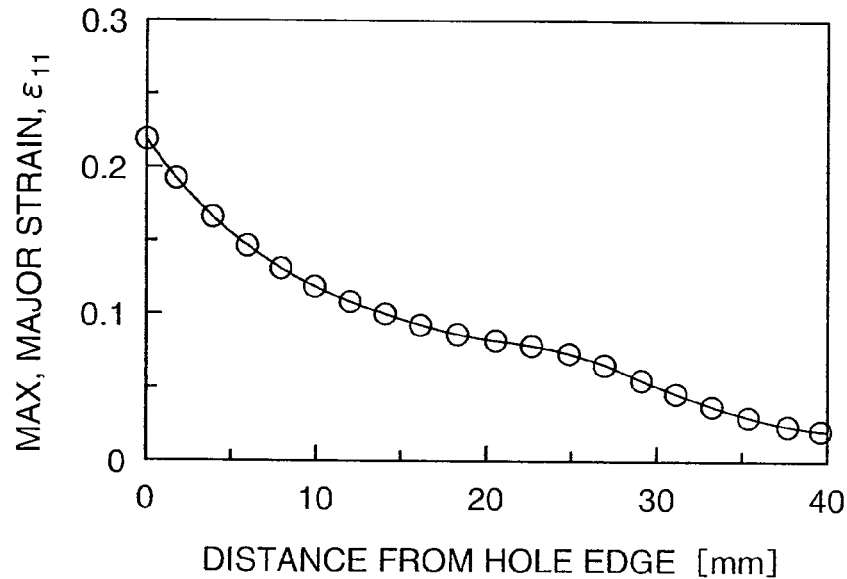
FIG. 18 is a graph for explaining an exemplary embodiment of an example of the present invention, and showing a relationship between a distance from a hole edge and a maximum major strain regarding the analysis result.
Figure 19:
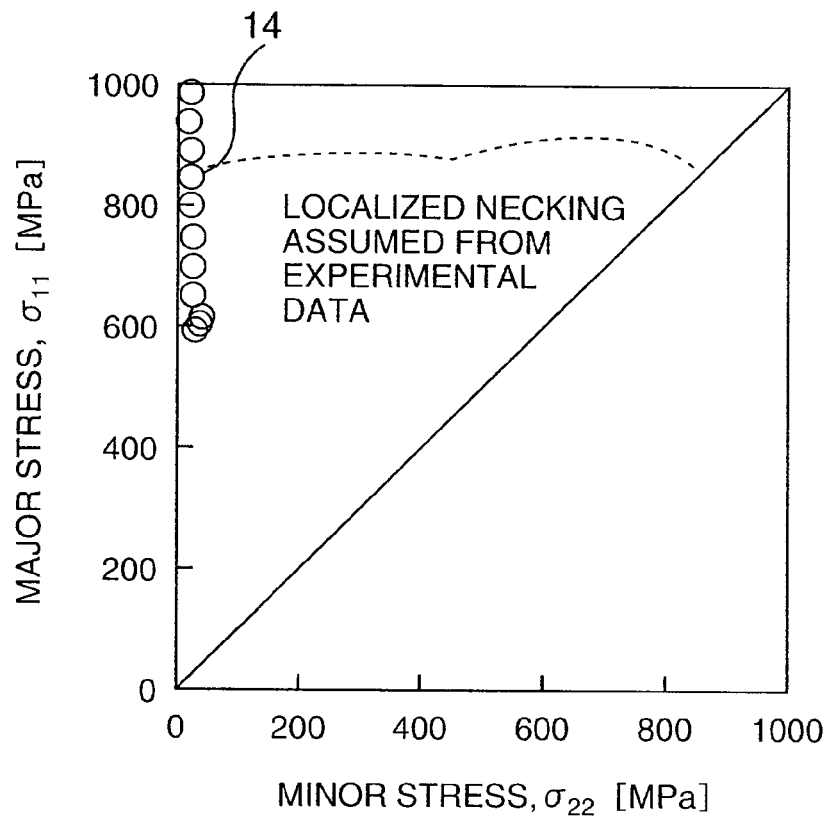
FIG. 19 is a diagram used for explaining an exemplary embodiment of an example of the present invention, and showing a relationship between a distance from a hole edge and a maximum major strain regarding the analysis result.

FIG. 17 shows exemplary simulation results of the stretch-flanging forming by the cylindrical flat-bottom punch, and FIG. 18 shows an exemplary relationship between the distance from the hole edge and the major strain. From FIGS. 17 and 18, it can be ascertained that a large strain is introduced to the hole edge of the cutting edge and that a large strain gradient exists inward from the edge hole. FIG. 19 shows a graph of an exemplary relationship between a stress history, in which a plastic strain obtained from the numerical simulation is converted into stress space and plotted for every forming height, and a "necking occurrence limit stress curve" obtained by converting into stress space a "necking occurrence limit curve", which is obtained by offsetting a forming limit curve measured on a proportional loading path so that the limit value in a plane strain becomes equal to n value. The stress at the hole edge reaches the necking occurrence limit stress curve at the forming height of 14 mm, which differs largely from the forming limit height of 18.5 mm measured actually by experiment. On the other hand, the fracture was evaluated in stress space with the fracture criterion being set to the hole expansion ratio. Note that the hole expansion ratio is defined by the following equation.

[Equation 10]

$$\lambda = \frac{d - d_0}{d_0} \quad (1)$$

Here, d is the hole diameter (mm) when the fracture occurs, and $d_0$ is the hole diameter (mm) of the steel sheet. For conversion into the criterion in stress space, a relational expression of the true strain $\epsilon_0$ of this hole expansion ratio, the equivalent stress $\sigma_{eq}$, and the equivalent plastic strain $\epsilon_{eq}$, for example the Swift's work-hardening law $$\sigma_{eq} = K(\epsilon_{eq} + \epsilon_0)^n \quad \text{[Equation 11]}$$

may be used. The equivalent plastic stress $\sigma_{eq}$ considering the strain path changes can be obtained using the equivalent plastic strain $\epsilon_{eq}$ obtained by integrating the equivalent plastic strain increment $d\epsilon_{eq}$ on a strain path and the work-hardening law.

Figure 20:
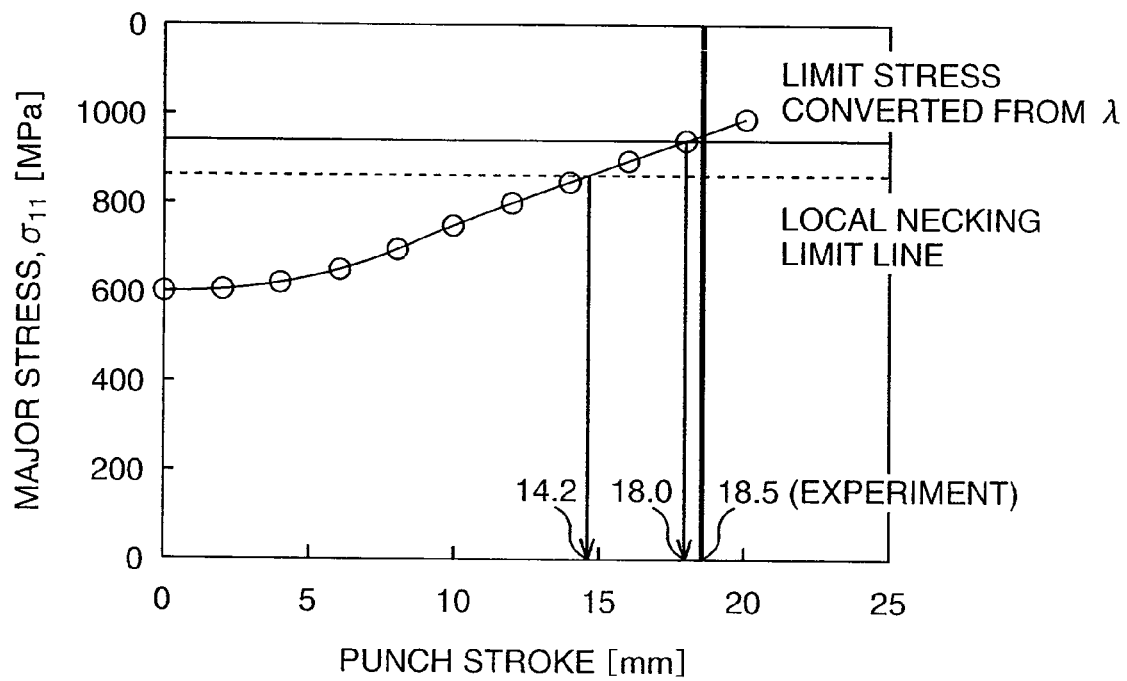
FIG. 20 is a graph used for explaining an exemplary embodiment of an example of the present invention, and showing a positional relationship between a stress history in a formation process obtained by a numerical simulation and a necking occurrence limit stress line.
Figure 21:
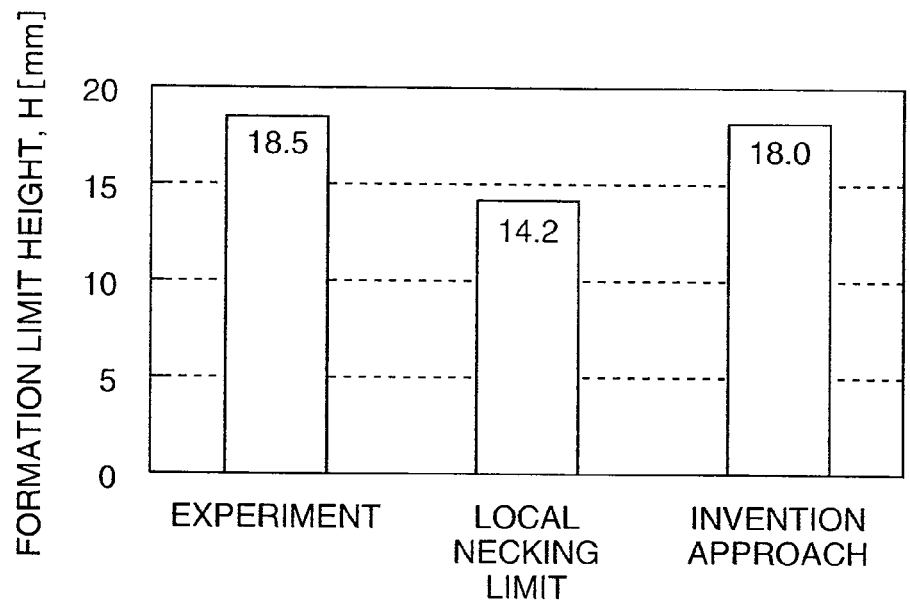
FIG. 21 is a diagram used for explaining an exemplary embodiment of an example of the present invention, and showing a positional relationship between a stress history in a formation process obtained by a numerical simulation and a necking occurrence limit stress curve, and a fracture determining criterion obtained by converting a hole expansion ratio into stress space.

FIGS. 20 and 21 show graphs of exemplary results of predicting a fracture by the exemplary embodiment of a method according to the present invention. When a conventional "necking occurrence limit stress curge" is used as the fracture criterion in a stretch—flanging forming, the forming limit height can be estimated low due to presence of a strain gradient inward from a cutting edge and a delay effect such that one position in the circumferential direction does not fracture when it satisfies the localized necking. However, the use of the criterion obtained by converting the hole expansion ratio into stress space for fracture determination may allow for a prediction of the fracture with a substantially good accuracy.

Example 3

Figure 22:
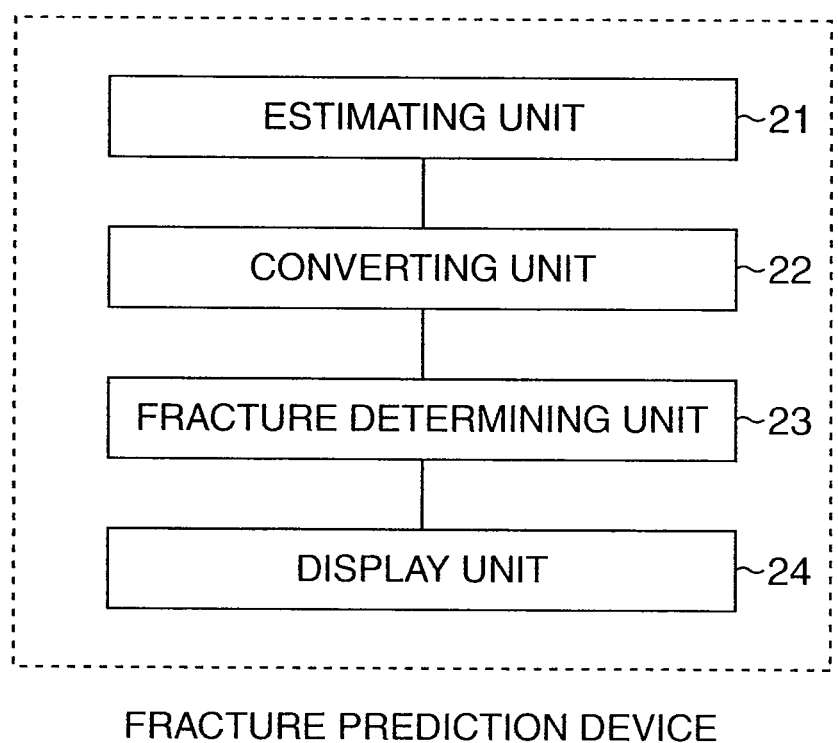
FIG. 22 is a block diagram showing a main structure of a fracture prediction device according to an exemplary embodiment of the present invention.

Hereinafter, in view of the above-described overall structure of the exemplary embodiment of the present invention, a specific example is described. For example, FIG. 22 is a block diagram showing a main structure of an exemplary embodiment of a fracture prediction device of the present invention according to this example. This exemplary fracture prediction device can be provided for predicting a presence of a fracture occurrence in a steel sheet in a process including one or more deformation path variations regarding a steel sheet constituted of a metal material. This exemplary device may include an estimating unit 21 estimating a fracture limit curve in strain space on a proportional loading path, a converting unit 22 converting the fracture limit curve in strain space obtained on the proportional loading path into a fracture limit curve in stress space, a fracture determining unit 23 determining presence of fracture occurrence with the fracture limit curve in stress space, and a display unit 24 displaying a determination result by the fracture determining unit 23, or the like.

For example, the estimating unit 21 may use the approximate equation $$\sigma_{eq} = (\epsilon_{eq} + \epsilon_0)^n \text{ or } \sigma_{eq} = C\epsilon^n_{eq} \quad \text{[Equation 12]}$$

of a stress-strain curve obtained for example from a uniaxial tensile test, a localized necking model

[Equation 13]

$$\varepsilon_1^* = \frac{n}{1+\rho}\left(\rho = \frac{d\varepsilon_2}{d\varepsilon_1} < 0\right)$$

and a diffuse necking model

[Equation 14]

$$\varepsilon_1^* = \frac{2n(\rho^2 + \rho + 1)}{(\rho+1)(2\rho^2 - p + 2)}(\rho \geq 0)$$

in combination to obtain a necking occurrence limit in strain space, and thereby estimates the fracture limit curve in strain space on the proportional loading path.

The estimating unit 1 may also be configured to obtain the necking occurrence limit in strain space using an approximate equation $$\sigma_{eq} = (\epsilon_{eq} + \epsilon_0)^n \text{ or } \sigma_{eq} C\epsilon^n_{eq} \quad \text{[Equation 15]}$$

of a stress-strain curve obtained from a uniaxial tensile test, a constitutive equation in which the direction of a plastic strain increment tensor depends on a stress increment tensor as a plastic strain increment law, a material parameter Kc defining the direction of the plastic strain increment tensor, and a Storen-Rice localized necking model, and estimate the fracture limit curve in strain space on the proportional loading path. For example, the estimating unit 21 may identify the material parameter Kc based on one or more measurement values of maximum fracture limit strain $\epsilon_1$ and minimum fracture limit strain $\epsilon_2$.

In this example, the case where the fracture limit curve in strain space is estimated theoretically using the estimating unit 21 is exemplified, but the fracture limit curve in strain space may be measured experimentally without using the estimating unit 21. For example, the fracture limit curve in strain space can be obtained, after a plurality of in-plane strain ratios regarding a thin plate are obtained by a proportional loading experiment, using measurement values of maximum fracture limit strain $\epsilon_1$ and minimum fracture limit strain $\epsilon_2$ in each of the strain ratios.

When converting the fracture limit curve in strain space into the fracture limit curve in stress space, the converting unit 22 may perform the above-described exemplary conversion using the vertical rule of yield surface as the plastic strain increment law. For example, as described above, the Mises' yield function

[Equation 16]

$$\varepsilon_{eq} = \sqrt{\frac{2}{3}\varepsilon_{ij}\varepsilon_{ij}}$$

is used, which is the relational expression of the equivalent plastic strain $\epsilon_{eq}$ and each strain component $\epsilon_{ij}$.

The fracture determining unit 23 can perform an exemplary evaluation by comparing the positional relationship between the fracture limit curve in stress space converted by the converting unit 21 and the strain state of each portion obtained from results of the simulation by the finite element method in a plastic deformation process. Such fracture determining unit 23 may determine that it is a fracture or that the risk of fracture is high when the strain in the deformation process reaches this limit strain. As an exemplary method of the numerical analysis, the dynamic explicit method can be used, which can be one of finite element methods. In this exemplary case, the plastic strain obtained by the exemplary dynamic explicit method may be converted into a stress and is compared with the fracture limit curve in stress space.

The exemplary fracture determining unit 23 may also be configured to convert a strain obtained from deformation conditions of a thin plate evaluated by experiment into a stress and evaluate quantitatively presence of fracture occurrence using the fracture limit curve in stress space, instead of performing the aforementioned simulation.

For example, in the case where a rapid deformation occurs in a thin plate as in a crash analysis of an automobile member, the fracture determining unit 23 can execute a numerical analysis considering the speed dependency of a flow stress in the thin plate, converts the plastic strain obtained from the numerical analysis to calculate the stress at the reference strain speed, and may compare this stress with the fracture limit curve in stress space corresponding to the reference strain rate.

Figure 23:
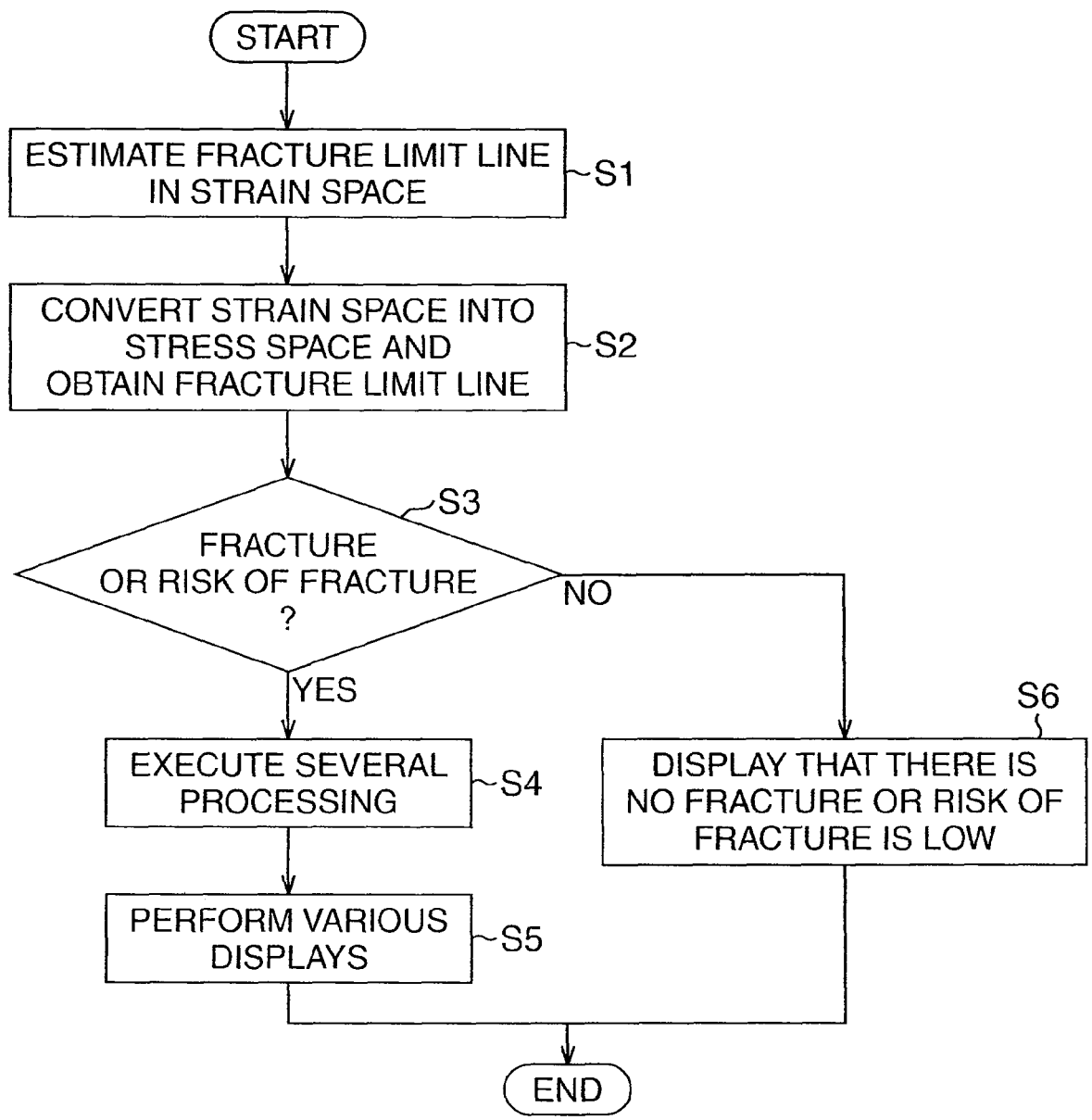
FIG. 23 is a flowchart showing exemplary steps when performing fracture prediction in a formation process of a thin plate constituted of a metal material, with a fracture prediction method according to an exemplary embodiment of the present invention.

FIG. 23 is a flowchart showing steps when performing fracture prediction in a forming process of a thin plate constituted of a metal material, with an exemplary embodiment of the fracture prediction method according to this example of the present invention. First, based on the material of the thin plate and the mechanical property values (t, YP, TS, E1, U.E1, r value, n-th power hardening law/Swift hardening law) which are inputted by the user, the estimating unit 21 estimates a fracture limit curve in strain space on a proportional loading path (step S1).

Subsequently, the converting unit 22 can convert the fracture limit curve in strain space measured experimentally into a fracture limit curve in stress space using the Mises' yield function, so as to create a stress FLD (step S2).

Subsequently, the fracture determining unit 23 may perform evaluation by comparing the positional relationship between the fracture limit curve in stress space converted by the converting unit 21 and the strain state of each portion obtained from results of the simulation by the finite element method (here, the dynamic explicit method) in a plastic deformation process, and can determine a fracture or the risk of fracture (step S3).

In step S3, when it is determined that the limit strain is reached and a fracture occurs in the thin plate or that the risk of fracture is high, the fracture determining unit 23 may execute the following several processing (step S4). The element ID, the thickness of the thin plate, the strain, and the stress information are outputted to a log file. Further, the element that has reached the criterion is erased, and the analysis after the fracture is continued.

Subsequently, the following various displays may be performed on the display unit 24 (step S5). The risk that a fracture occurs in the thin plate is contour displayed by a scalar amount. Further, the stress history of the fracture risk portion in stress space and the criterion are displayed. The risk of occurrence of a crease in the thin plate is contour displayed together. Here, the risk of fracture may be displayed with respect to dispersion (average value, lower limit value) within the standard of shipment test values.

On the other hand, when it is determined in step S3 that there is no possibility of occurrence of a fracture or that the risk thereof is low, an indication about this is displayed on the display unit 24 in step S6.

Figure 24:
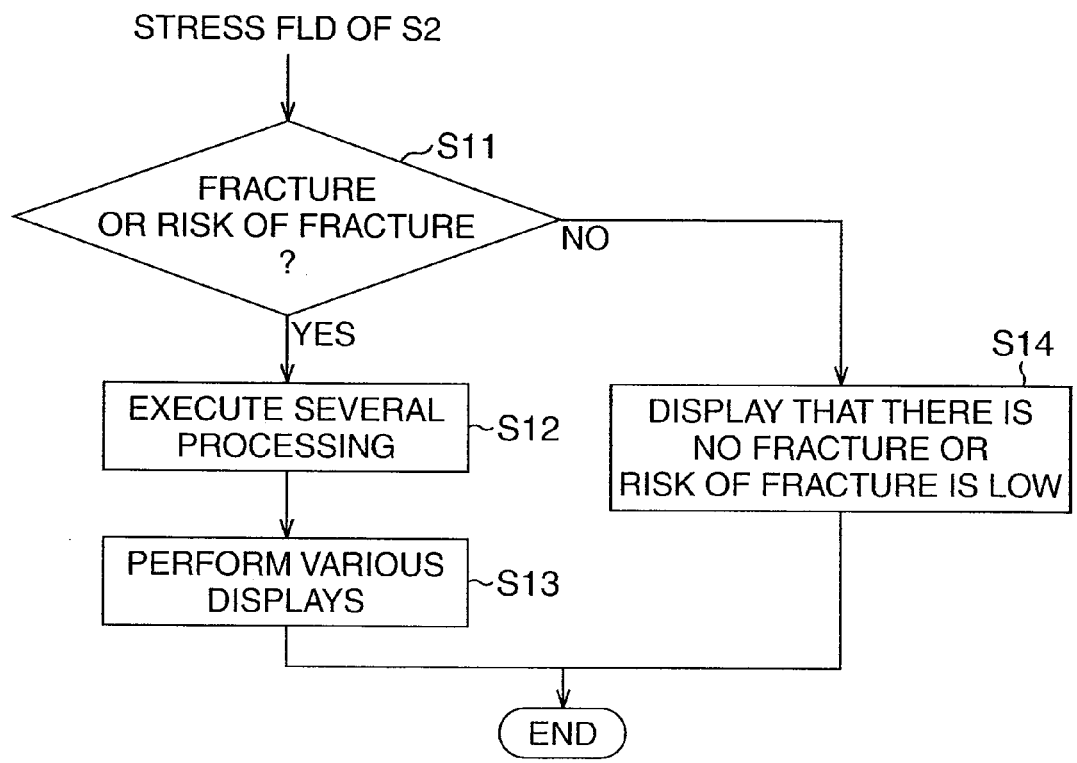
FIG. 24 is a flowchart showing steps when performing fracture prediction in a crash process, continued from the fracture prediction in a formation step of FIG. 23, with the fracture prediction method according to an exemplary embodiment of the present invention.

FIG. 24 is a flowchart showing exemplary steps when performing the fracture prediction in the crash process, continued from the fracture prediction in the formation step of FIG. 23, with the exemplary fracture prediction method according to this example of the present invention.

In this case, the stress FLD created in step S2 of FIG. 23 can be inherited and used. Then, the fracture determining unit 23 may execute a numerical analysis considering the strain rate dependency of a deformation stress in the thin plate, converts the plastic strain obtained from the numerical analysis to calculate the stress at the reference strain rate, and compares this stress with the fracture limit curve in stress space corresponding to the reference strain rate, thereby determining a fracture or the risk of fracture (step S11).

In this step S11, the fracture determining unit 23 can inherit deformation conditions of the thin plate evaluated by the numerical analysis in the formation process of FIG. 23 as an initial condition of the numerical analysis in the crash process. The deformation conditions are thinning and an equivalent plastic strain or thinning, an equivalent plastic strain, a stress tensor and a strain tensor.

In step S11, when it is determined that a fracture occurs in the thin plate or that the risk of fracture is high, the fracture determining unit 23 may execute the following several processing (step S12). The element ID, thinning, the strain, and the stress information are outputted to a log file. Further, the element that has reached the criterion is erased, and the analysis after the fracture is continued.

Subsequently, the following various displays may be performed on the display unit 24 (step S13). The risk that a fracture occurs in the thin plate is contour displayed by a scalar amount. Further, the stress history of the fracture risk portion in stress space and the criterion are displayed. The risk of occurrence of a crease in the thin plate is contour displayed together. Here, the risk of fracture may be displayed with respect to dispersion (average value, lower limit value) within the standard of shipment test values.

On the other hand, when it is determined in step S11 that there is no possibility of occurrence of a fracture in the thin plate or that the risk thereof is low, an indication about this can be displayed on the display unit 24 in step S14.

As explained above, according to this example, when determining the fracture limit of a thin plate in a process including one or more deformation path variations, it is possible to obtain the fracture limit curve easily and efficiently and determine the fracture limit with high prediction accuracy. Thus, the risk of fracture upon press forming or crash can be evaluated quantitatively, thereby realizing efficient and highly precise development of an automobile body optimized the material, the forming, and the body structure.

Second Exemplary Embodiment

Conventionally, the margin against a fracture is often evaluated by a thinning, but due to popularization of numerical simulations and advancement in functions of post-processing software, fracture evaluation methods using a forming limit diagram (FLD) are started to be used widely. The FLD can be obtained by an experiment such as the Nakajima method. However, such a method is complicated, and it is difficult to construct a database for various types of steel sheet menus and thickness. Thus, several prediction approaches have been proposed.

For example, in post-processing functions of general-purpose software, there can be incorporated a method (as described in Journal of the Japan Society for Technology of Plasticity, 45, 123, 2004) in which a Keeler's thickness correction empirical rule is added to the Hill's localized necking model and the Swift's diffuse necking model. However, prediction values obtained with these theories may allow for a prediction for aluminum or mild steel with relatively high accuracy, but for steel sheets with tensile strength of 440 MPa class or higher, they are overestimated on the uniaxial tension side and underestimated on the equi-biaxial stretching side. Thus, they are not suitable for current development of an automobile body in which high-strength steel sheets are mainly used.

Further, the FLD is known to vary largely depending on a deformation path. High prediction accuracy cannot be expected therefrom as a method of evaluating a fracture in a plastic deformation process, in which the deformation path varies largely as in crash of an automobile body part subjected to press-forming or pre-deformation in press-forming. However, recently Kuwabara et al. (e.g., described in Journal of the Japan Society for Technology of Plasticity, 45, 123, 2004; and CAMP-ISIJ 17, 1063, 2004) verified by experiment and analysis that, using a fracture limit curve expressed in stress space with an aluminum extruded material or mild steel being the subject, the fracture limit can be represented almost uniquely without depending on the path of deformation. This knowledge relates to aluminum or mild steel and is not clarified for steel sheets with tensile strength of 440 MPa class or higher.

Accordingly, detailed experiments have been conducted on high strength steels with tensile strength of 440 MPa or higher, and the following has been determined.

(1) The FLD of strain space obtained on a proportional loading path can be predicted highly accurately using a stress-strain curve obtained from a uniaxial tensile test and the thickness of a virgin material or a stress-strain curve, the thickness of a virgin material, and a parameter Kc defining stress increment dependency. Thus, an FLD database of strain space for various types of steel sheet menus and thickness can be constructed easily and simply.

(2) Fracture determination in a process including one or more deformation path variations is possible by converting the FLD of strain space obtained on the proportional loading path into stress space and determining a fracture in stress space.

EXAMPLES

The second exemplary embodiment of the present invention will be explained in detail based on several examples.

Example 1

First, an exemplary method of measuring the FLD of strain space experimentally is described. The fracture limit strain can be measured by a proportional loading experiment with a steel sheet constituted of a metal material having mechanical property values and material parameters shown in Table 1 below being the subject. Here, t represents the thickness of a thin plate, YP represents proof strength, TS represents ultimate tensile strength, U.El represents uniform elongation, El represents total elongation, $r_m$ represents average r value (indicating a Lankford value and is expressed by $r_m=(r_0+2r_{45}+r_{90})/4$ where r value in the rolling direction is $r_0$, r value in the 45° direction with respect to the rolling direction is r45, and r value in the 90° direction with respect to the rolling direction is r90), and K, $\epsilon_0$, n represent material parameters obtained when a stress-strain curve obtained from a uniaxial tensile test is fitted in a function expression:

$$\sigma_{eq}=K(\epsilon_{eq}+\epsilon_0)^n \quad [\text{Equation 17}]$$

For the fracture limit strain in a proportional loading experiment, a fracture strain was measured with a scribed circle diameter being 6 mm by a uniaxial tension, the Nakajima method (ball head extrusion using a Teflon (registered trademark) sheet), and a hydraulic bulge test.

Figure 25:
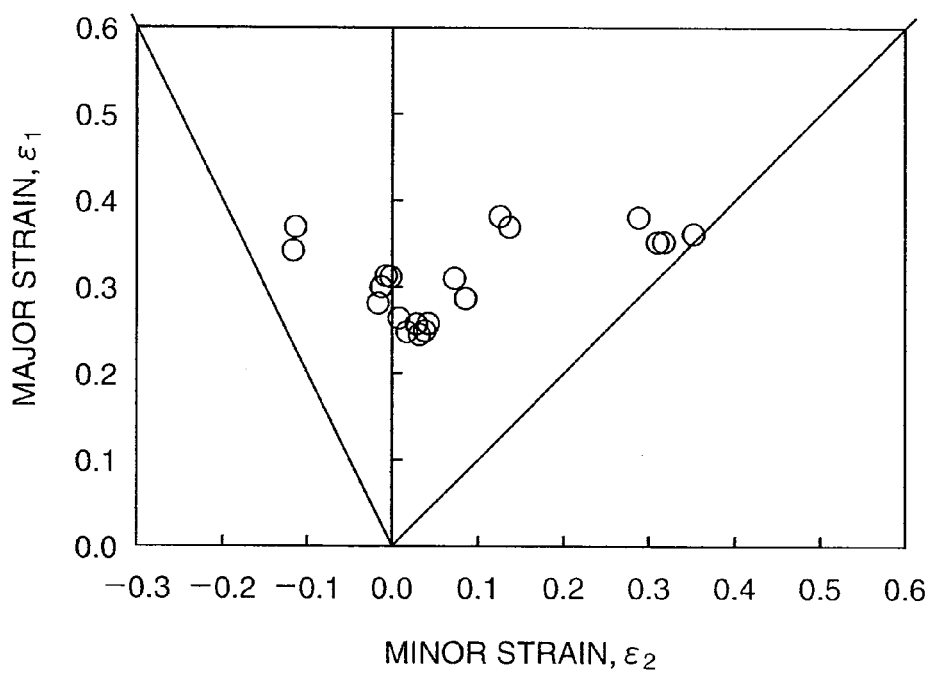
FIG. 25 is a graph used for explaining an exemplary embodiment of the present invention, and is a forming limit diagram (FLD) measured by experiment.

FIG. 25 shows a graph of the FLD including the fracture limit curve in strain space measured by the above experiment.

TABLE 4

| t/mm | YP | TS | U. El | El | $r_m$ | K | $\epsilon_0$ | n |
|------|-----|-----|-------|----|-------|-----|--------|-------|
| 1.2  | 460 | 598 | 12    | 23 | 1.00  | 937 | 0.0108 | 0.157 |

(UNIT t: mm; YP, TS, K: MPa; El, U. El: %)

Next, an exemplary embodiment of a method of estimating the fracture limit curve in strain space theoretically from mechanical properties is described. For example, as an exemplary FLD estimation method, there may be a combining usage of the Hill's localized necking model and the Swift's diffuse necking model, the Storen-Rice model (see, e.g., J. Mech. Phys. Solids, 2, 421, 1975), etc., and it can be obtained by correcting the influence of a thickness by the Keeler's empirical rule. An exemplary embodiment of a specific calculation method is described as follows. First, data are sampled for obtaining $$\sigma_{eq}=f(\epsilon_{eq}) \quad [\text{Equation 18}]$$

As a test method, a uniaxial tensile test is simple and favorable. From a stress-strain curve obtained from the uniaxial tensile test, material parameters may be determined by fitting in a function expression including suitable material parameters as $$\sigma_{eq}=f(\epsilon_{eq}) \quad [\text{Equation 19}]$$

Using the n-th power hardening law often used in a numerical simulation of a thin plate with high accuracy of approximation, they can be expressed by $$\sigma_{eq}C\epsilon_{eq}^n \quad [\text{Equation 20}]$$

As the fracture limit strain, using the n-th power hardening law and the Mises' yield function

[Equation 21]
$$\sigma_{eq}=\sqrt{\frac{3}{2}\sigma_{ij}\sigma_{ij}}$$

for the yield curved surface, the Hill's localized necking can be given by

[Equation 22]
$$\varepsilon_1^* = \frac{n}{1+\rho}$$

and the Swift's diffuse necking can be given by

[Equation 23]
$$\varepsilon_1^* = \frac{2n(\rho^2 + \rho + 1)}{(\rho+1)(2\rho^2 - \rho + 2)}$$

However, the Hill's theory is used in the range of

[Equation 24]
$$\rho = \frac{d\varepsilon_2}{d\varepsilon_1} \leq 0$$

since the localized necking cannot be obtained with the biaxial extension, and the Swift's diffuse necking is applied in the range of ρ>0. FIG. 25 shows a graph of the FLD in which the influence of the thickness in the theoretically calculated localized necking limit is corrected using the Keeler's empirical rule

[Equation 25]
$$\varepsilon_1^* = \ln\left[1 + \frac{n}{0.21}(0.233 + 0.141 t_0)\right]$$

with the thickness being $t_0$ (mm).

The Swift's diffuse necking has a tendency to estimate the fracture limit small in the vicinity of the equi-biaxial stretching, and is needed to be improved. Therefore, it may be preferable to use the Storen-Rice model which is extended from the Hill's localized necking model based on the bifurcation theory. By the Storen-Rice model, when an increment display of the total strain theory for the Mises' yield curved surface is used for the n-th power hardening law and the yield curved surface, the fracture limit strain in the range of ρ≥0 can be given by

[Equation 26]
$$\varepsilon_1^* = \frac{3\rho^2 + n(2+\rho)^2}{2(2+\rho)(1+\rho+\rho^2)}$$

Figure 26:
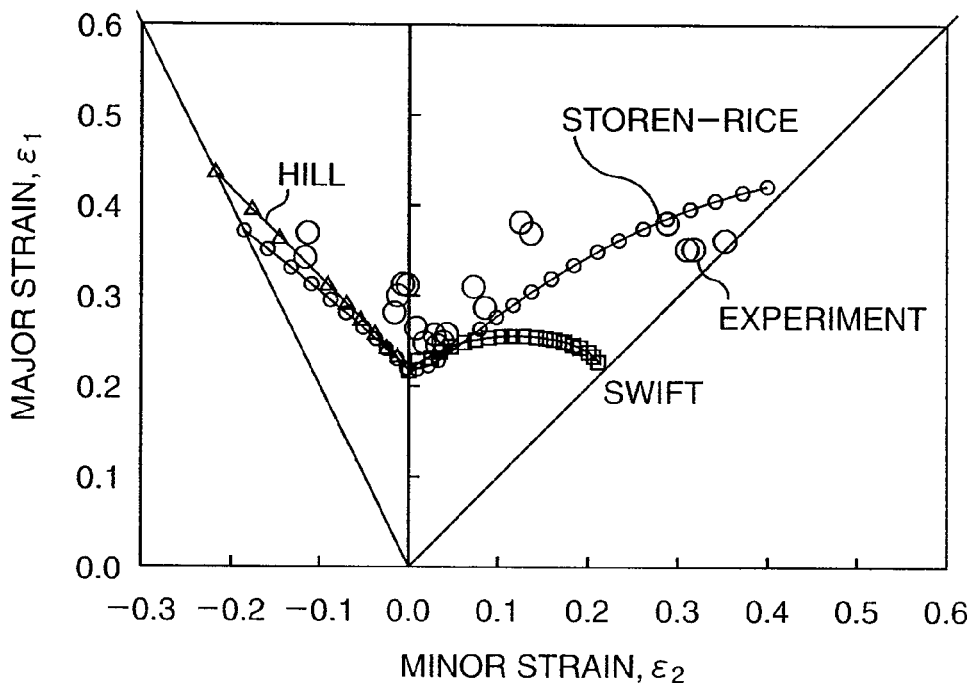
FIG. 26 is a graph used for explaining an exemplary embodiment of the present invention, and is a forming limit diagram (FLD) considering the influence of a steel thickness using a Keeler's steel thickness correction rule with respect to a plastic unstableness limit curve predicted by Hill-Swift theory and Storen-Rice model.

FIG. 26 shows a graph of the FLD including the fracture limit curve in strain space calculated using the Storen-Rice model. Although there can be seen larger improvement of the prediction accuracy than in the Swift's diffuse necking model, it is difficult to assure sufficient accuracy. Ito et al, Transactions of the Japan Society of Mechanical Engineers, Series A, 54, 1617, 1998 describes a constitutive equation in which the direction of a plastic strain increment tensor depends on a stress increment tensor, so as to overcome a drawback such that in the normality rule with the Mises' isotropic yield function being a plastic potential, the stress increment tensor and the plastic strain increment tensor do not correspond one to one, and the plastic strain increment direction does not follow a rapid variation in the stress direction. In this exemplary constitutive equation, the parameter Kc defining the stress increment dependency of the plastic strain increment is necessary, but the physical background of Kc can be unclear, and a deriving method of the parameter is not described.

Accordingly, as results of performing experiments and studies on high strength steel sheets of 440 MPa to 980 MPa classes shown in Table 5 below, the following exemplary results have been achieved.

(1) The FLD can be predicted with high accuracy when the material parameter Kc is identified based on measurement values of fracture limit major strain $\epsilon_1$, and fracture limit minor strain $\epsilon_2$ in the equi-biaxial stretching deformation.

(2) Kc does not depend on a thickness, and hence Kc that is minimally required may be obtained for each of tensile strength of a material, strengthening mechanism of a steel sheet, and the like.

Figure 27:
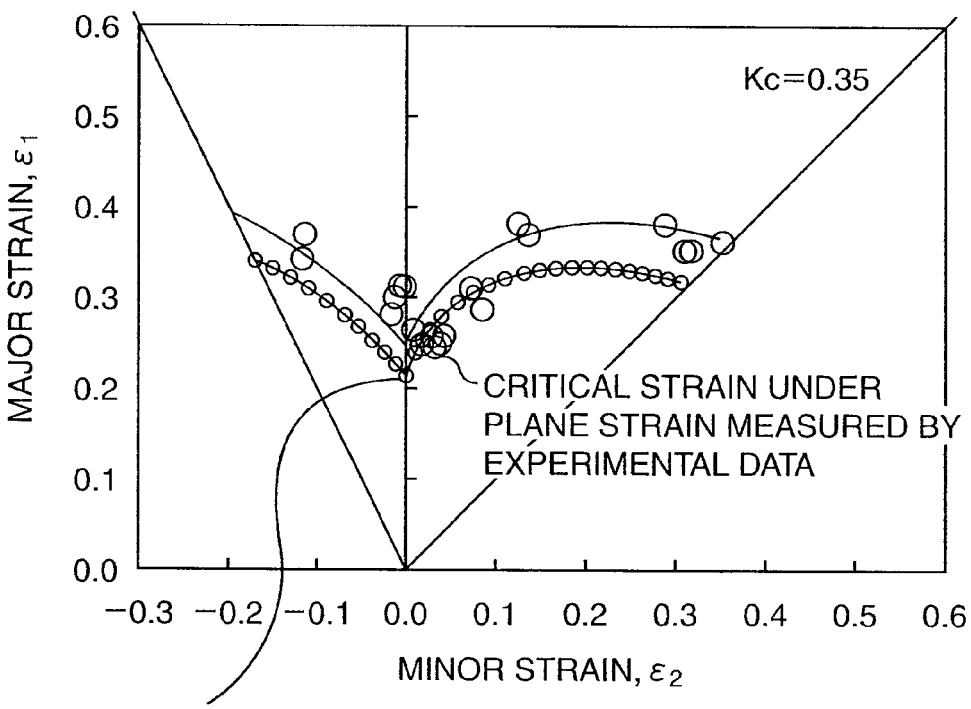
FIG. 27 is a graph used for explaining an exemplary embodiment of the present invention, and a forming limit diagram (FLD) predicted using a stress increment dependency law based on the Storen-Rice model.

FIG. 27 shows a graph of the FLD calculated by obtaining Kc for the precipitation strengthened steel sheet of 590 MPa class shown in Table 5 by the above-described exemplary method and using a stress increment dependency law based on the Storen-Rice model. It is possible to obtain a higher prediction accuracy by correction using the fracture limit strain $\epsilon_1^*$ in a plane strain measured by experiment instead of the Keeler's thickness correction rule. However, in an aspect that the FLD database for various types of steel sheet menus and thickness can be constructed only by stress-strain curves by uniaxial tensile tests of materials, it may be efficient to use the Keeler's thickness correction rule.

TABLE 5

| MATERIAL | t/ mm | YP/ MPa | TS/ MPa | U. El (%) | El (%) |
|---|---|---|---|---|---|
| A: 440 MPa CLASS SOLID SOLUTION HARDENDED STEEL | 1.2 | 368 | 460 | 18 | 35 |
| B: 590 MPa CLASS PRECIPITATION HARDENED STEEL | 1.2 | 460 | 598 | 12 | 23 |
| C: 590 MPa CLASS Dual Phase steel | 2.0 | 462 | 600 | 12 | 23 |
| D: 780 MPa CLASS Dual Phase steel | 2.0 | 490 | 840 | 10 | 19 |
| E: 980 MPa CLASS Dual Phase steel sheet | 2.0 | 710 | 1010 | 8 | 14 |

(UNIT t: mm; YP, TS, MPa; El, U. El: %)

Exemplary Method of Converting Fracture Limit Curve in Strain Space into Fracture Limit Curve in Stress Space With the steel sheets shown in Table 4 being the subjects, the fracture limit curve on a proportional loading path can be predicted by the above method, and for the fracture limit curve under strain path changes, after an tension of 10% in the rolling direction is performed as first deformation, a fracture strain was measured by the uniaxial tension, the Nakajima method (e.g., ball head extrusion using a Teflon (registered trademark) sheet), and a hydraulic bulge test so that the direction of about 90° degrees from the primary extension direction is the maximum principal stress.

Conversion from a strain to a stress becomes possible by assuming (1) incompressibility, (2) Mises' yield function, (3) material hardening law with isotropy, (4) normality rule, and (5) membrane state of stress.

An exemplary embodiment of a method for converting the fracture limit curve in strain space into stress space is described. The FLD of strain space is a diagram showing a major strain $\epsilon_{11}$ giving the fracture limit for each minor strain $\epsilon_{22}$, and a thickness strain $\epsilon_{33}$ can be obtained by them and the constant volume law $$(\epsilon_{33} - (\epsilon_{11} + \epsilon_{22}))$$  [Equation 27]

Generally, in the constitutive law used in a formation analysis or crash analysis, there is used the isotropic hardening law assuming that an equivalent plastic stress $\sigma_{eq}$ is the unique function of an equivalent plastic strain $\epsilon_{eq}$ regardless of the path of deformation, and can be represented using the Swift's work-hardening law as $$\sigma_{eq}=(\epsilon_{eq}\epsilon_0)^n \quad \text{[Equation 28]}$$

As the function of work hardening, for example, the high-degree polynomial expression of an equivalent plastic strain or another form may be used, but it is preferable to use the Swift's equation, which is highly precise in approximation and is used frequently in a numerical simulation of a thin steel sheet. Using the Mises' yield function on a yield curved surface for example, the equivalent plastic strain $\epsilon_{eq}$ can be represented as

[Equation 29]

$$\varepsilon_{eq} = \sqrt{\frac{2}{3}\varepsilon_{ij}\varepsilon_{ij}}$$

In addition, a high-degree anisotropic yield function may be used as necessary, but it has many parameters and requires considering the direction in a plate surface while processing, and hence provides insufficient improvement in precision even though it is complicated. Thus, in practice, the yield function assuming planer isotropy is sufficient.

Next, a deviatoric stress component $\sigma_{ij}'$ can be obtained by the normality rule

Figure 28:
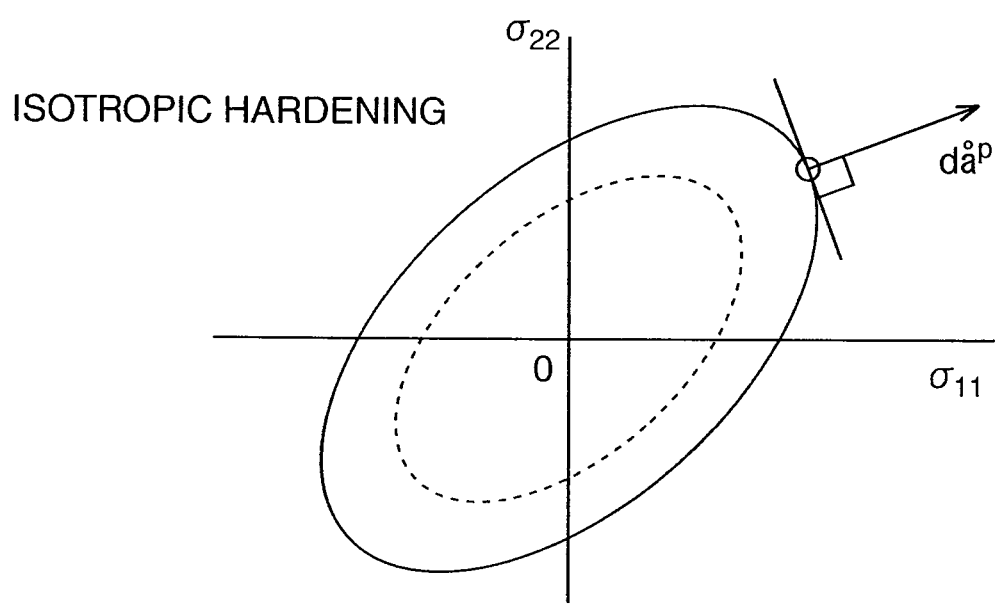
FIG. 28 is a diagram used for explaining an exemplary embodiment of the present invention, and conversion from a strain into a stress.

[Equation 30]

$$\sigma'_{ij} = \sigma_{eq}\frac{\partial \varepsilon_{eq}}{\partial \varepsilon_{ij}}$$

of the plastic strain increment with respect to the yield curved surface shown in FIG. 28. Finally, by assuming the plane stress ($\sigma_{33}=0$), the stress component $\sigma_{ij}$ can be obtained from $$\sigma_{ij}=\sigma_{ij}'-\sigma_{33}'\delta_{ij} \quad \text{[Equation 31]}$$

Figure 29:
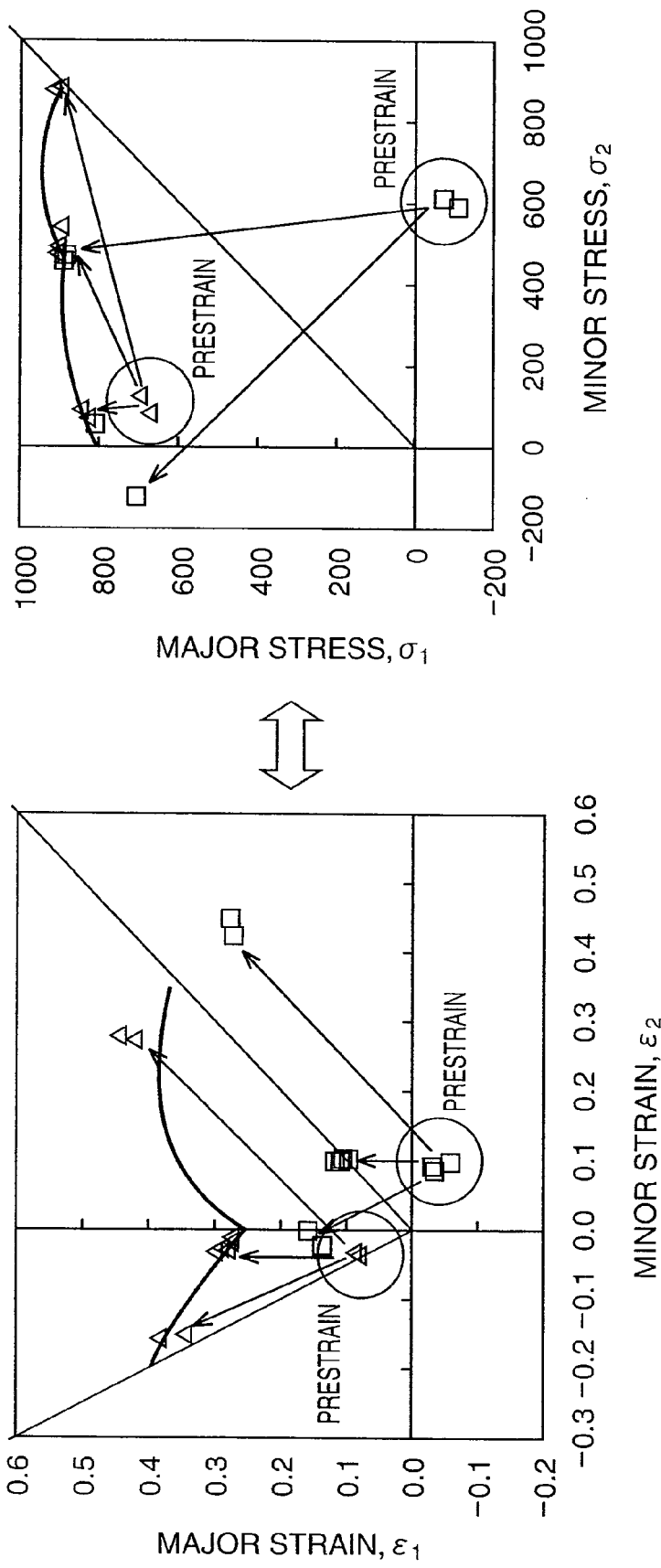
FIG. 29 are graphs for explaining an exemplary embodiment of the present invention, and showing that, while an FLD of strain space depends on a deformation path and a fracture limit thereof varies largely, a fracture limit curve in stress space can be expressed by a single curve.

FIG. 29 shows graphs of exemplary results of conversion of the FLD predicted by the above-described method and the fracture limit strain under the deformation path variation measured by experiment into stress space respectively. For example, in the FLD of strain space, the fracture limit varies largely depending on the deformation path, but the fracture limit curve expressed in stress space can be represented by a single fracture limit curve regardless of the deformation path. Therefore, for the fracture limit curve of a material passing through a plurality of plastic deformation paths, the FLD of strain space obtained on a proportional loading path may be converted into stress space. In practice, for the database of fracture limit curves for various types of steel sheet menus and thickness, a fracture limit curve can be obtained by obtaining the forming limit diagram (FLD) in strain space from the stress-strain curve obtained from a uniaxial tensile test and the thickness of a material, and converting this into stress space.

Further, according to the exemplary embodiments of the present invention, as a result of performing experiments and studies on the high-strength steel sheets of 440 MPa to 980 Mpa classes shown in Table 5, regardless of the tensile strength of a material or strengthened mechanism, single fracture limit curves can be produced in a wide range. Using these exemplary fracture limit curves expressed in stress space, fracture evaluation in a plastic deformation process in which the deformation path varies largely, as in a crash of an automobile body part subjected to press-forming or pre-deformation in press-forming, can be predicted with high accuracy.

Example 2

Further, an exemplary embodiment of a method of measuring a hole expansion ratio in strain space experimentally according to the present invention is described. The provided material can be Dual Phase steel sheet with a thickness of 1.2 mm produced by cold-rolled and continuously annealed, and has mechanical properties shown in Table 6. The mechanical properties may be obtained using JIS-5 specimens according to JIS Z 2201 cut out in the rolling direction of the steel sheets and a screw-driven tester at a crosshead speed of 10 mm/min (strain speed $3\times10^{-3}$/s).

TABLE 6

| MECHANICAL TEST VALUES OF PROVIDED MATERIAL | | | | | | | | |
|---|---|---|---|---|---|---|---|---|
| t/ mm | YP/ MPa | TS/ MPa | U. El (%) | El (%) | K/MPa | $\epsilon_0$ | n' | $r_m$ |
| 1.2 | 354 | 614 | 17 | 30 | 1109 | 0.0070 | 0.230 | 0.89 |

(YP: PROOF STRENGTH, TS: ULTIMATE TENSILE STRENGTH, U. El: UNIFORM ELONGATION, El: TOTAL ELONGATION, $r_m$: LANKFORD VALUE)

Figure 30:
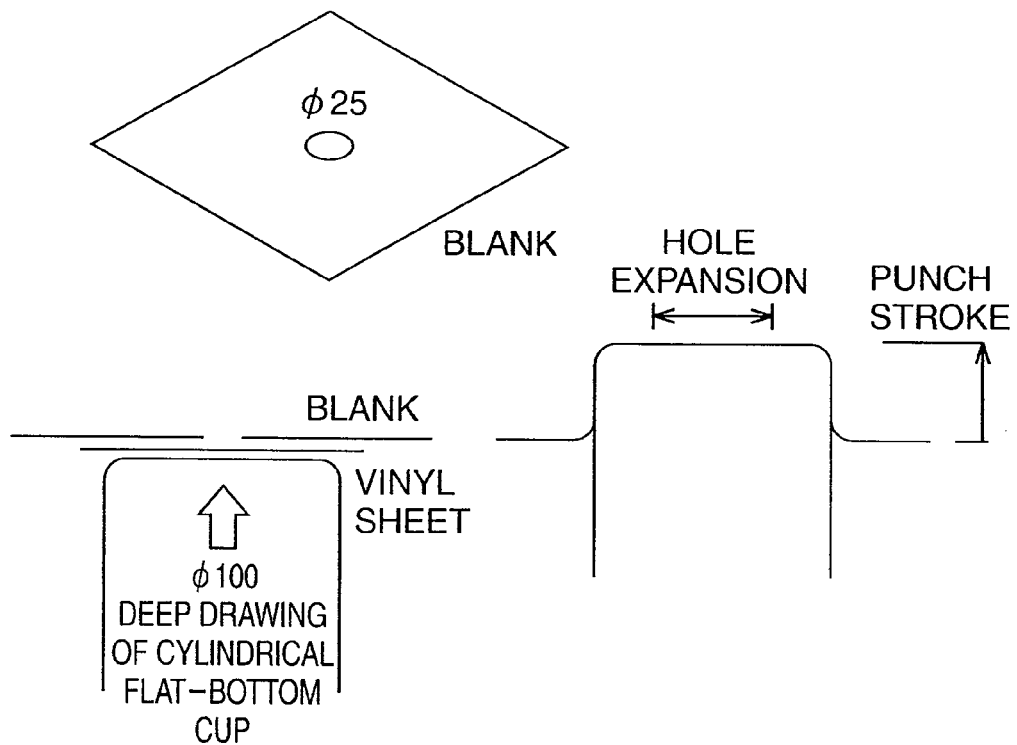
FIG. 30 is a diagram for explaining an exemplary embodiment of the present invention, and an experiment method of the exemplary embodiment.

First, the virgin material was sheared by the size of 200 mm×200 mm, and a hole with a diameter of 25 mm was punched through a center portion using a punch and a die. This steel sheet with a hole in the center was subjected to formation (Teflon sheet lubrication) using a flat-bottom punch with a diameter of 100 mm and a die shoulder R of 15 mm until a fracture occurs at a hole edge, and the hole diameter and the formation limit height when the fracture occurs were measured. The overview of the experiment is shown in FIG. 30. Here, when d is the hole diameter (mm) when the fracture occurs, and do is the hole diameter (mm) of the steel sheet, a stretch strain of the hole edge (hole expansion ratio) is defined by the following equation.

[Equation 32]

$$\lambda = \frac{d - d_0}{d_0} \quad (1)$$

Assuming isotropy, in strain space of a major strain and a minor strain, the fracture limit can be expressed using this hole expansion ratio as follows.

[Equation 33]

$$\epsilon_{11}=\ln(\lambda-1), \epsilon_{22}-0.5\epsilon_{11} \quad (2)$$

Next, an exemplary embodiment of a method of converting from the mechanical properties into the fracture limit in stress space according to the present invention is described. First, data are sampled for obtaining $\sigma_{eq}=f(\epsilon_{eq})$. As a test method, a uniaxial tensile test is simple and favorable. From a stress-strain curve obtained from the uniaxial tensile test, material parameters may be determined by fitting in a function expression including suitable material parameters as $\sigma_{eq}=f(\epsilon_{eq})$. Normally, in the constitutive law used in a forming analysis or crash analysis, there is used the isotropic hardening law assuming that an equivalent plastic stress $\sigma_{eq}$ is the unique function of an equivalent plastic strain $\epsilon_{eq}$ regardless of the path of deformation, and can be represented using the Swift's work-hardening law as

[Equation 34]

$$\sigma_{eq} = (\epsilon_{eq} + \epsilon_0)^n \quad (3)$$

As the function of work hardening, for example, the high-degree polynomial expression of an equivalent plastic strain or another form may be used, but it is preferable to use the Swift's expression, which is highly precise in approximation and is used frequently in a numerical simulation of a thin steel sheet.

A thickness strain $\epsilon_{33}$ can be obtained by Equation (3) and the constant volume law,

[Equation 35]

$$\epsilon_{33} = -(\epsilon_{11} + \epsilon_{22}) \quad (4)$$

Using the Mises' yield function on a yield curved surface for example, the equivalent plastic strain $\epsilon_{eq}$ can be represented as

[Equation 36]

$$\varepsilon_{eq} = \sqrt{\frac{2}{3}\varepsilon_{ij}\varepsilon_{ij}} \quad (5)$$

In addition, a high-degree anisotropic yield function may be used as necessary, but it has many parameters and requires considering the direction in a plate surface while processing, and hence provides insufficient improvement in precision even though it is complicated. Thus, in practice, the yield function assuming planer isotropy is sufficient.

Further, for conversion into stress space, a relational expression of the true strain $\epsilon_0$ of this hole expansion ratio, the equivalent stress $\sigma_{eq}$, and the equivalent plastic strain $\epsilon_{eq}$, for example the Swift's work-hardening law

[Equation 37]

$$\sigma_{eq} = K(\epsilon_{eq} + \epsilon_0)^n \quad (6)$$

may be used. Next, a deviatoric stress component $\sigma_{ij}'$ can be obtained by the normality rule

[Equation 38]

$$\sigma_{ij}' = \sigma_{eq} \frac{\partial \varepsilon_{eq}}{\partial \varepsilon_{ij}} \quad (7)$$

of the plastic strain increment with respect to the yield curved surface shown in FIG. 28. Finally, by assuming the plane stress ($\sigma_{33} = 0$), the stress component $\sigma_{ij}$ can be obtained from

[Equation 39]

$$\sigma_{ij} = \sigma_{ij}' - \sigma_{33}'\delta_{ij} \quad (8)$$

Figure 31:
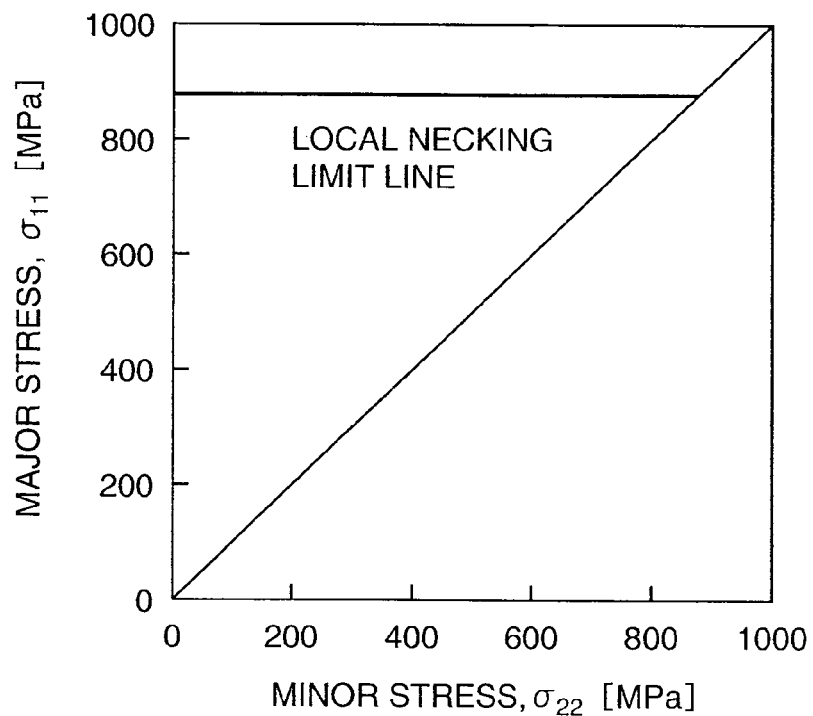
FIG. 31 is a graph for explaining an exemplary embodiment of the present invention, and showing a fracture limit stress line expressing a hole expansion ratio in stress space.

FIG. 31 shows a graph of the fracture limit stress line obtained with the above exemplary method. When a conventional fracture limit curve is used as the fracture limit (fracture criterion) in a stretch flange deformation, the formation limit height is estimated low due to presence of a strain gradient inward from a cutting edge portion and a delay effect such that one position in the circumferential direction does not fracture when it satisfies the localized necking. Using the fracture limit stress line obtained by the above exemplary method for fracture determination, the fracture can be predicted with good accuracy.

Example 3

Figure 32:
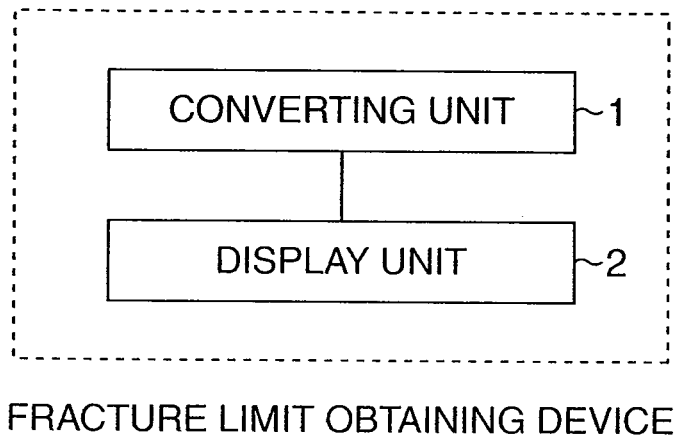
FIG. 32 is a block diagram showing a main structure of a fracture limit obtaining device according to a first example.

FIG. 32 shows a block diagram showing a main structure of the exemplary embodiment of a fracture limit obtaining device according to Example 1. This exemplary fracture limit obtaining device can be provided for determining the fracture limit of a steel sheet in a process including one or more deformation path variations regarding a steel sheet, and may be structured to include a converting unit 1 converting a fracture limit curve in strain space obtained on a proportional loading path into a fracture limit curve in stress space, and a display unit 2 displaying the fracture limit curve in stress space obtained by the converting unit 1 as a stress FLD.

In this example, the fracture limit curve in strain space can be measured experimentally. Specifically, the fracture limit curve in strain space can be obtained, after a plurality of in-plane strain ratios regarding a steel sheet are obtained by a proportional loading experiment, using measurement values of fracture limit major strain $\epsilon_1$ and fracture limit minor strain $\epsilon_2$ in each of the strain ratios.

When converting the fracture limit curve in strain space into the fracture limit curve in stress space, the converting unit 1 may perform the above-described exemplary conversion using the normality rule of a plastic strain increment in which a plastic strain increment direction is defined in the direction perpendicular to a yield surface. For example, as described above, the Mises' yield function

[Equation 40]

$$\varepsilon_{eq} = \sqrt{\frac{2}{3}\varepsilon_{ij}\varepsilon_{ij}}$$

may be used, which is the relational expression of the equivalent plastic strain $\epsilon_{eq}$ and each strain component $\epsilon_{ij}$.

Figure 33:
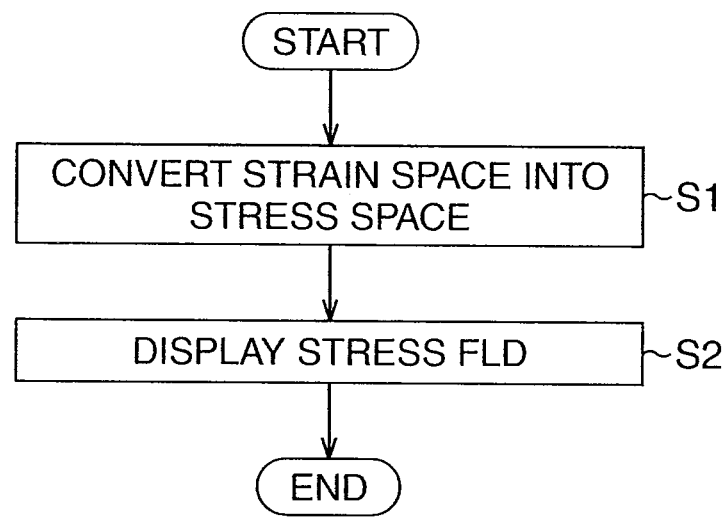
FIG. 33 is a flowchart showing steps of fracture limit obtaining method according to the first example.

FIG. 33 shows a flowchart showing steps of a fracture limit obtaining the exemplary embodiment of a method according to Example 1. In this example, as described above, the fracture limit curve in strain space can be measured experimentally. First, in conjunction with the type of a steel sheet inputted by the user, the converting unit 1 may convert a fracture limit curve in strain space measured experimentally into a fracture limit curve in stress space using the Mises' yield function for example (step S1).

Subsequently, the fracture limit curve in stress space obtained in step S1 can be displayed as a stress FLD on the display unit 2 (step S2).

As described above, according to this example, when determining the fracture limit of a thin plate in a process including one or more deformation path variations, it is possible to obtain the fracture limit curve easily and efficiently and determine the fracture limit with high prediction accuracy. With this example, the risk of fracture upon press forming or crash can be evaluated quantitatively, thereby enabling efficient and highly precise development of an automobile body optimized the material, the forming, and the body structure.

Example 4

Figure 34:
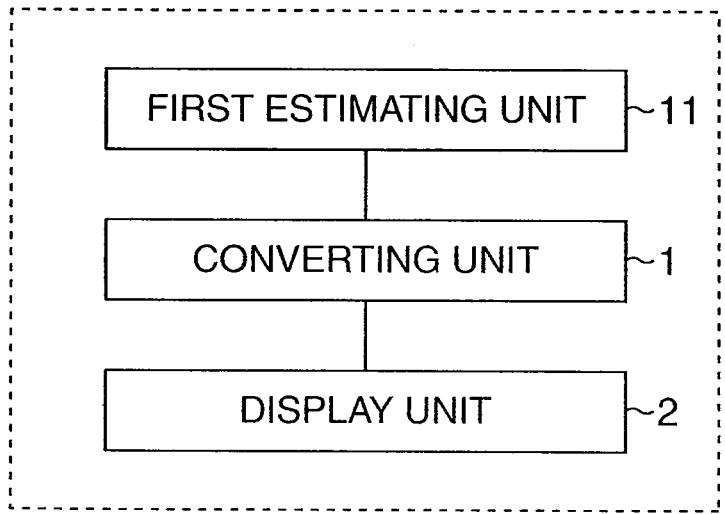
FIG. 34 is a block diagram showing a main structure of a fracture limit obtaining device according to a second example.

FIG. 34 shows a block diagram showing a main structure of an exemplary embodiment of a fracture limit obtaining device according to Example 2. The same components as those in FIG. 32 of Example 1 are given the same numerals, and detailed explanation thereof is omitted for that reason. This exemplary fracture limit obtaining device can be provided for determining the fracture limit of a steel sheet in a process including one or more deformation path variations regarding a steel sheet, and may be structured to include a first estimating unit 11 estimating a fracture limit curve in strain space on a proportional loading path, a converting unit 1 converting the obtained fracture limit curve in strain space into a fracture limit curve in stress space, and a display unit 2 displaying the fracture limit curve in stress space obtained by the converting unit 1 as a stress FLD.

The first estimating unit 11 may use the approximate equation

[Equation 41]

$$\sigma_{eq} = C\epsilon_{eq}^n$$

of a stress-strain curve obtained from a uniaxial tensile test, a localized necking model

[Equation 42]

$$\varepsilon_1^* = \frac{n}{1+\rho}\left(\rho = \frac{d\varepsilon_2}{d\varepsilon_1} < 0\right)$$

and a diffuse necking model

[Equation 43]

$$\varepsilon_1^* = \frac{2n(\rho^2 + \rho + 1)}{(\rho+1)(2\rho^2 - \rho + 2)}(\rho \geq 0)$$

in combination to obtain a necking occurrence limit in strain space, and thereby can estimate the fracture limit curve in strain space on the proportional loading path as described above.

Figure 35:
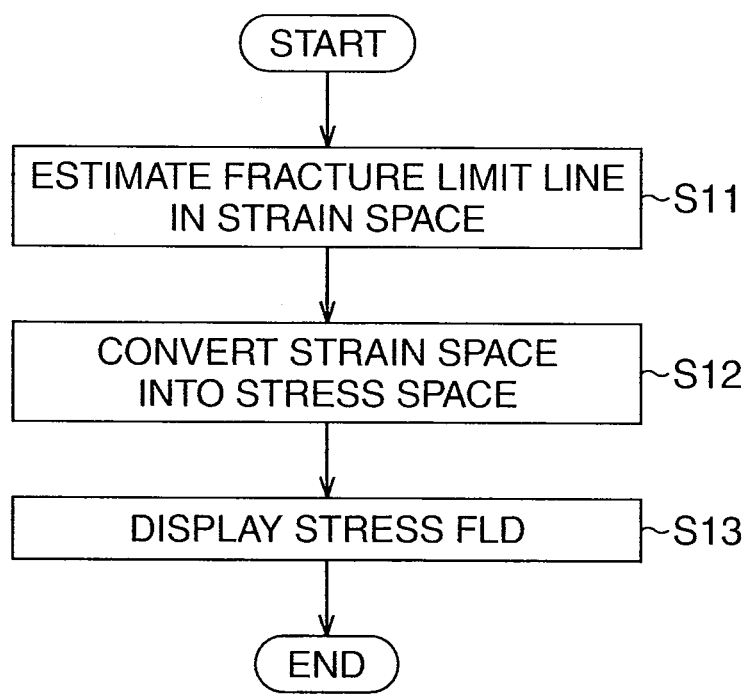
FIG. 35 is a flowchart showing steps of a fracture limit obtaining method according to the second example.

FIG. 35 shows a flowchart showing steps of an exemplary embodiment of a fracture limit obtaining method according to Example 1. First, e.g., the user inputs the material and the mechanical property values (t, YP, TS, E1, U.E1, r value, n-th power hardening law/Swift hardening law) of a thin plate.

The first estimating unit 11 can estimate a fracture limit curve in strain space on a proportional loading path based on the mechanical property values inputted by the user (Step S11).

Subsequently, the converting unit 1 may convert the fracture limit curve in strain space estimated by the first estimating unit 11 into a fracture limit curve in stress space using the n-th power hardening law/Swift hardening law inputted as the mechanical properties, and for example the Mises' yield function or the like (Step S12). Subsequently, the fracture limit curve in stress space obtained in step S1 may be displayed as a stress FLD on the display unit 2 (step S13).

In addition, the exemplary embodiment of the method may also be arranged such that the strain FLD is estimated from a database (t, YP, TS, E1, U.E1, r value, strain-stress multiple linear data) of shipping test values, and the stress FLD is calculated from the shipping test values (upper limit value and lower limit value in a quality dispersion distribution within a predetermined standard, and the mean value in the quality dispersion distribution).

As described above, according to this example, when determining the fracture limit of a steel sheet in a process including one or more deformation path variations, it is possible to obtain the fracture limit curve easily and efficiently and determine the fracture limit with high prediction accuracy. By this example, the risk of fracture upon press forming or crash can be evaluated quantitatively, thereby enabling efficient and highly precise development of an automobile body optimized the material, the forming, and the body structure.

(Modification Example)

Figure 36:
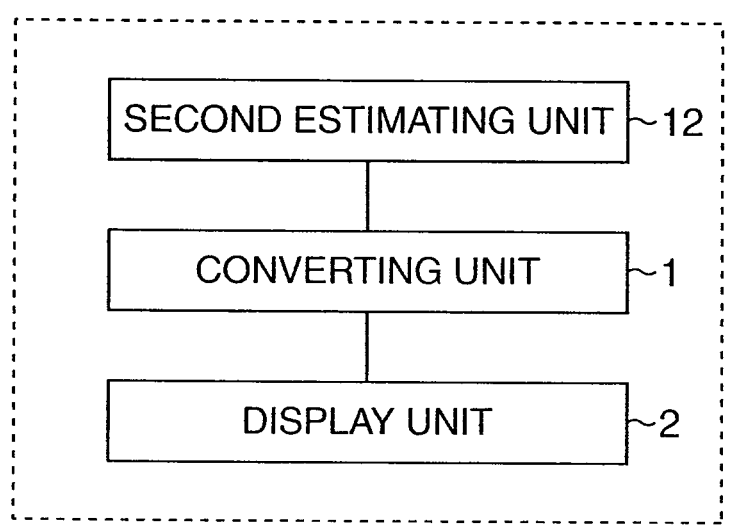
FIG. 36 is a block diagram showing a main structure of a fracture limit obtaining device according to a modification example of the second example.

In particular, a modification example of Example 2 is described. In this modification example, as shown in FIG. 36, in the fracture limit obtaining device of Example 2, a second estimating unit 12 can be provided instead of the first estimating unit 11.

The second estimating unit 12 may estimate the fracture limit curve in strain space on a proportional loading path similarly to the first estimating unit 11, and can obtain, as described above, a necking occurrence limit in strain space using an approximate equation

[Equation 44]

$$\sigma_{eq} = K(\epsilon_{eq} + \epsilon_0)^n \text{ or } \sigma_{eq} = C\epsilon_{eq}^n$$

of a stress-strain curve obtained from a uniaxial tensile test, a constitutive equation in which the direction of a plastic strain increment tensor depends on a stress increment tensor as a plastic strain increment law, a material parameter Kc defining the direction of the plastic strain increment tensor, and a Storen-Rice localized necking model, and estimates the fracture limit curve in strain space on the proportional loading path. The second estimating unit 12 may identify, as described above, the material parameter Kc based on one or more measurement values of fracture limit major strain $\epsilon_1$ and fracture limit minor strain $\epsilon_2$.

As described above, according to this example, better and adequate accuracy can be obtained for fracture prediction as compared to Example 2, and the fracture limit curve can be obtained more easily and efficiently, thereby allowing to determine the fracture limit with high prediction accuracy.

Other Exemplary Embodiments Applying the First, Second Embodiments

The exemplary functions of the respective components (e.g., except the display unit 4) constituting the fracture prediction devices according to the above-described examples and the like can be realized by operation of a program product stored in a RAM or ROM of a computer. Similarly, the respective steps of the exemplary embodiments of the fracture prediction method and the fracture limit obtaining method (e.g., see steps S1 to S6 of FIG. 23, steps S11 to S14 of FIG. 24, and so on, steps S1 and S2 of FIG. 33, steps S11 to S13 of FIG. 35, and so on) can be realized by operation of a program product stored in a RAM or ROM of a computer. This exemplary program product and an exemplary computer readable/computer accessible recording medium recording the program product are further exemplary embodiments of the present invention.

For example, the aforementioned program product can be provided to a computer by recording in a recording medium such as CD-ROM, for example, or by transmitting via various types of transmission media. As the recording medium recording the program product, other than the CD-ROM, it is possible to use a flexible disk, a hard disk, a magnetic tape, a magneto-optical disk, a non-volatile memory card, or the like. Further, as a transmission medium of the program product, a communication medium in a computer network system for supplying program information by propagating as a carrier wave can be used. Here, the computer network is a LAN, a WAN such as the Internet, a radio communication network, or the like, and the communication media is a wired line such as an optic fiber, a wireless line, or the like.

Further, the exemplary embodiment of the program product of the present invention is not only one such that the functions of the above-described embodiments are realized by a computer executing the supplied program product. For example, when the exemplary program product cooperates with the OS (operating system), another application, or the like working on the computer to realize the functions of the above-described embodiments, such exemplary program product configures the system, according to another exemplary embodiment of the present invention, to perform the procedures described herein. Furthermore, according to another exemplary embodiment of the present invention, all or some of processing of the exemplary program product is performed by a function expansion board or a function expansion unit of the computer to realize the functions of the above-described embodiments.

Figure 37:
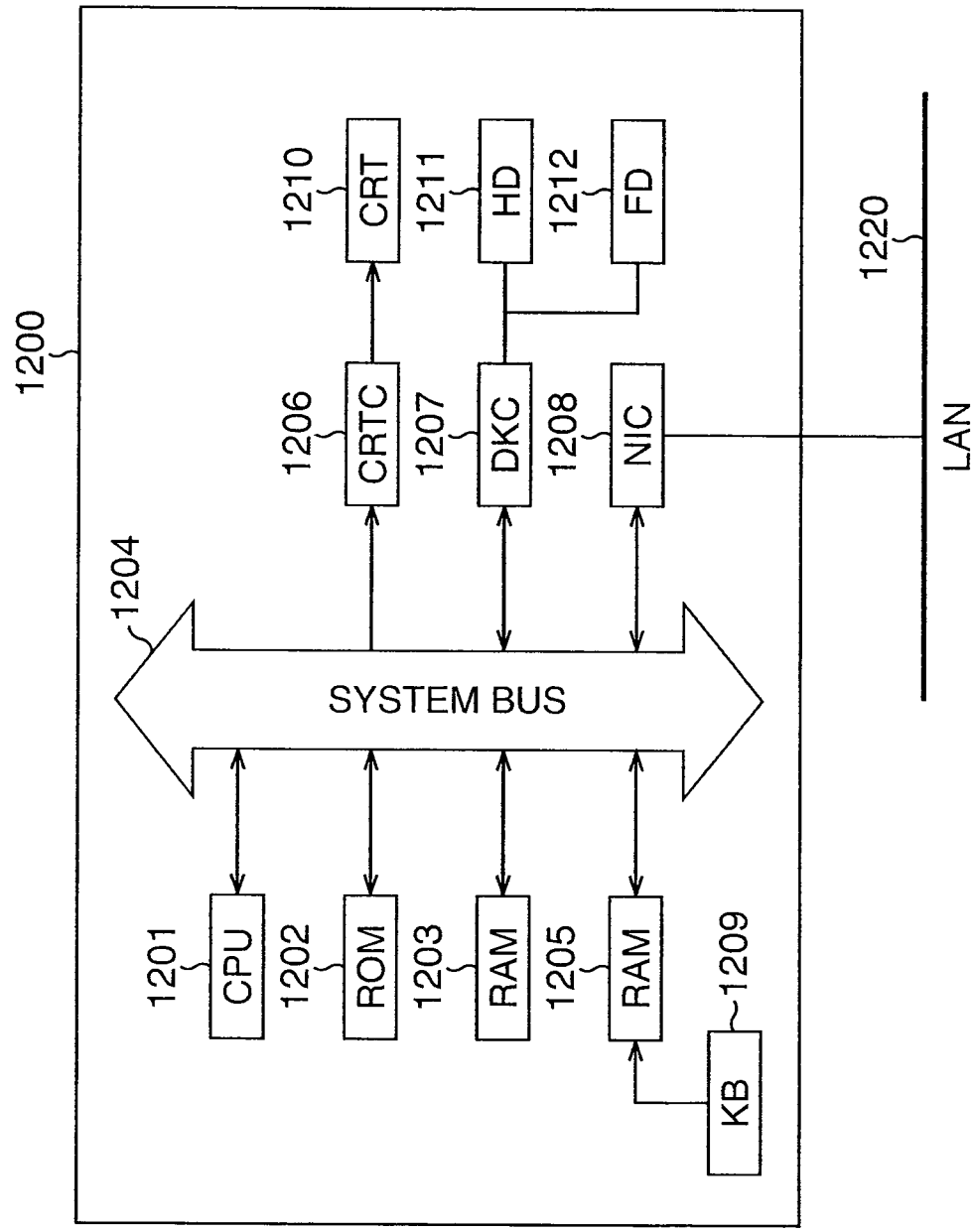
FIG. 37 is a schematic diagram showing an internal structure of a personal user terminal device.

For example, FIG. 37 shows a schematic diagram illustrating an exemplary internal structure of a personal user terminal device in accordance with another exemplary embodiment of the present invention. In particular, FIG. 37 provides a numeral 1200 which denotes a personal computer (PC) including a CPU 1201. The PC 1200 executes device control software which is stored in a ROM 1202 or a hard disk (HD) 1211 or supplied by a flexible disk drive (FD) 1212. This PC 1200 controls devices connected to a system bus 1204 in an integrated manner.

By the CPU 1201 of the PC 1200 and the program product stored in the ROM 1202 or the hard disk (HD) 1211, the exemplary procedures or the like of steps S1 to S6 in FIG. 23 of the example and steps S11 to S14 in FIG. 24, steps S1 and S2 of FIG. 33, steps S11 to S13 of FIG. 35 can be realized.

Numeral 1203 denotes a RAM and functions as a main memory, a work area, or the like for the CPU 1201. Numeral 1205 denotes a keyboard controller (KBC) and controls an instruction input from a keyboard (KB) 1209, a not-shown device, or the like.

Numeral 1206 denotes a CRT controller (CRTC) and controls display on the CRT display (CRT) 1210. Numeral 1207 denotes a disk controller (DKC). The DKC 1207 controls access to the hard disk (HD) 1211 storing a boot program, a plurality of applications, edit files, user files, a network administration program, and so on, and to the flexible disk (FD) 1212. Here the boot program is a start-up program, a program starting execution (operation) of hardware and/or software of a personal computer.

Numeral 1208 denotes a network interface card (NIC) and carries out bidirectional exchange of data via a LAN 1220 with a network printer, another network device, or another PC.

INDUSTRIAL APPLICABILITY

According to exemplary embodiments of the present invention, when predicting presence of fracture occurrence in a thin plate in a process including one or more deformation path variations, it is possible to obtain the fracture limit curve easily and efficiently and predict the presence of fracture occurrence with high prediction accuracy. Thus, the risk of fracture upon press forming or crash can be evaluated quantitatively, thereby realizing efficient and highly precise development of an automobile body optimized the material, the forming, and the body structure.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements, media and methods which, although not explicitly shown or described herein, embody the principles of the invention and are thus within the spirit and scope of the present invention. In addition, all publications referenced herein above are incorporated herein by reference in their entireties.

What is claimed is:

1. A non-transitory computer-accessible medium having instructions thereon for evaluating a particular fracture limit and a fracture likelihood of a thin plate which is a solid thin plate that includes a metal material, wherein when a hardware processing arrangement executes the instructions, the hardware processing arrangement is configured to perform procedures comprising:

convert a first fracture limit curve which changes depending on a deformation path in a forming limit diagram of strain space obtained by an estimating unit into a single second fracture limit curve in a stress space when performing a particular procedure of predicting a fracture occurrence in the solid thin plate in a plastic deformation process according to at least one deformation path variation;

predict a presence of a fracture occurrence during the particular procedure using the second fracture limit curve measured at a single reference strain rate which is a quasi-static strain rate, said single reference strain rate which is the quasi-static strain rate being a strain rate in the range of 0.001/s to 1/s, wherein the second fracture limit curve measured at said single reference strain rate indicates a fracture limit of the solid thin plate when the solid thin plate is subjected to the reference strain rate before the solid thin plate is fractured, and wherein the second fracture limit curve measured at said single reference strain rate is used as a fracture limit for fracture determination of the solid thin plate, and wherein a hole expansion ratio is used as a criterion for a fracture and deformation conditions of the solid thin plate evaluated by numerical analysis that employs a dynamic explicit method; and convert a plastic strain of the solid thin plate obtained by the dynamic explicit method, into a stress by a numerical simulation post-processing, and compare said stress with the second fracture limit curve in stress space, to predict whether a fracture would occur in the solid thin plate.

2. The computer-accessible medium according to claim 1, wherein, when predicting the fracture occurrence in the thin plate corresponding to each of a plurality of the plastic deformation processes, deformation conditions of the thin plate evaluated by a numerical analysis in the plastic deformation process in a preceding stage are inherited as initial conditions of the numerical analysis in the plastic deformation process in a succeeding stage.

3. The computer-accessible medium according to claim 2, wherein the deformation conditions of the thin plate include a thickness of the thin plate and an equivalent plastic strain or the thickness, an equivalent plastic strain, a stress tensor and a strain tensor.

4. The computer-accessible medium according to claim 1, wherein the plastic deformation process in a preceding stage is a formation process of the thin plate, and the plastic deformation process in a succeeding stage is a crash process of the thin plate.

5. The computer-accessible medium according to claim 1, wherein, in the converting procedure, the first fracture limit curve is obtained from an experiment.

6. The computer-accessible medium according to claim 1, wherein, in the converting procedure of converting, the first fracture limit curve is estimated theoretically from mechanical property values.

7. The computer-accessible medium according to claim 6, wherein the hardware processing arrangement is further configured to convert a necking start line in the strain space into the stress space to obtain the second fracture limit curve.

8. The computer-accessible medium according to claim 1, wherein, in the predicting procedure, a strain obtained from deformation conditions of the thin plate evaluated by an experiment is converted into a stress, and the presence of the fracture occurrence is evaluated quantitatively using the second fracture limit curve.

9. The computer-accessible medium according to claim 1, wherein, in the predicting procedure, deformation conditions of the thin plate are evaluated by a numerical analysis, and the numerical analysis is executed considering a speed dependency of a deformation stress of the thin plate, a plastic strain obtained from the numerical analysis is converted to determine a stress at a reference strain rate, and the stress is compared with the second fracture limit curve corresponding to the reference strain rate.

10. The computer-accessible medium according to claim 1, wherein the hardware processing arrangement is further configured to determine a fracture prediction of a material using a criterion obtained by converting a hole expansion ratio obtained from a hole expansion test into the stress space.

11. The computer-accessible medium according to claim 1, wherein, during the converting procedure, a normality rule of a plastic strain increment is used in which a plastic strain increment direction is defined in a direction perpendicular to a yield curved surface.

12. The computer-accessible medium according to claim 11, wherein, when using the normality rule of the plastic strain increment, a relational expression of an equivalent plastic strain $\varepsilon_{eq}$ and each strain component $\varepsilon_{ij}$ uses the following formula:

$$\varepsilon_{eq} = \sqrt{\frac{2}{3}\varepsilon_{ij}\varepsilon_{ij}}.$$

13. The computer-accessible medium according to claim 11, wherein a stretch strain obtained from a hole expansion test is converted into the stress space, and a fracture is determined in the stress space.

14. The computer-accessible medium according to claim 1, wherein the hardware processing arrangement is further configured, when obtaining the first fracture limit curve on a proportional loading path, and after a plurality of in-plane strain ratios regarding the thin plate are obtained by a proportional loading experiment, to use measurement values of fracture limit major strain $\varepsilon_1$ and fracture limit minor strain $\varepsilon_2$ in each of the strain ratios.

15. The computer-accessible medium according to claim 1, wherein, when the fracture limit curve in strain space is obtained on a proportional loading path, the following is usable in combination to obtain a necking occurrence limit in the strain space:

i. an approximate equation of a stress-strain curve obtained from a uniaxial tensile test, as follows $\sigma_{eq} = C\varepsilon^n_{eq}$, ii. a localized necking model, as follows:

$$\varepsilon_1^* = \frac{n}{1+\rho}\left(\rho = \frac{d\varepsilon_2}{d\varepsilon_1} < 0\right), \text{ and}$$

iii. a diffuse necking model, as follows:

$$\varepsilon_1^* = \frac{2n(\rho^2 + \rho + 1)}{(\rho+1)(2\rho^2 - \rho + 2)}(\rho \geq 0),$$

wherein $\sigma_{eq}$ represents an equivalent stress, $\varepsilon_{eq}$ represents an equivalent plastic strain, C represents a work-hardening rate, n represents a work-hardening index, $\varepsilon_1^*$ represents a fracture limit major strain giving the fracture limit in plane-strain deformation.

16. The computer-accessible medium according to claim 1, wherein, when the fracture limit curve in strain space is obtained on a proportional loading path, the following is usable to obtain a necking occurrence limit in the strain space:

i. an approximate equation of a stress-strain curve obtained from a uniaxial tensile test, as follows:

$\sigma_{eq} = K(\varepsilon_{eq} + \varepsilon_0)^n$ or $\sigma_{eq} = C\varepsilon^n_{eq}$, ii. a constitutive equation in which a direction of a plastic strain increment tensor depends on a stress increment tensor as a plastic strain increment law, iii. a material parameter Kc defining the direction of the plastic strain increment tensor, and iv. a Storen-Rice localized necking model, wherein $\sigma_{eq}$ represents an equivalent stress, $\varepsilon_{eq}$ represents an equivalent plastic strain, $\varepsilon_0$ represents a true strain, C represents a work-hardening rate, and n represents a work-hardening index.

17. The computer-accessible medium according to claim 16, wherein, with the necking occurrence limit being a reference, the following are usable to obtain a fracture limit strain in the strain space:

i. a thickness $t_0$ (mm) of the thin plate, ii. a stress-strain curve obtained from a uniaxial tensile test, and iii. a thickness correction equation, as follows:

$$\varepsilon_1^* = \ln\left[1 + \frac{n}{0.21}(0.233 + 0.141t_0)\right],$$

where $\varepsilon_1^*$ represents a fracture limit major strain giving the fracture limit in plane-strain deformation.

18. The computer-accessible medium according to claim 16, wherein the material parameter Kc is identified based on one or more measurement values of a fracture limit major strain $\varepsilon_1$ and a fracture limit minor strain $\varepsilon_2$.

19. The computer-accessible medium according to claim 15, wherein, with the necking occurrence limit being a reference, the following are usable to obtain a fracture limit strain in the strain space:

i. a thickness $t_0$ (mm) of the thin plate, ii. a stress-strain curve obtained from a uniaxial tensile test, and iii. a thickness correction equation, as follows:

$$\varepsilon_1^* = \ln\left[1 + \frac{n}{0.21}(0.233 + 0.141 t_0)\right].$$

20. The computer-accessible medium according to claim 1, wherein the thin plate is constituted of a high strength material with tensile strength of about at least 440 MPa class.

21. The computer-accessible medium according to claim 1, wherein
the second fracture limit curve in stress space does not depend on the deformation path of the solid thin plate, when the deformation path of the solid thin plate varies among a plurality of different deformation paths.

22. A method for designing an automobile body part using a thin plate which is a solid thin plate that includes a metal material, the method comprising:
using a computer processing arrangement, performing a fracture prediction procedure for the solid thin plate, the procedure comprising:
with a converting unit, converting a first fracture limit curve which changes depending on a deformation path in forming a limit diagram of strain space obtained by a estimating unit into a single second fracture limit curve in the stress space when performing a particular procedure of determining a fracture occurrence in the thin plate in a plastic deformation procedure according to at least one deformation path variation;
with a fracture determining unit, predicting during the particular procedure a presence of the fracture occurrence using the second fracture limit curve measured at a single reference strain rate which is a quasi-static strain rate, said single reference strain rate which is the quasi-static strain rate being a strain rate in the range of 0.001/s to 1/s, wherein the second fracture limit curve measured at said single reference strain rate indicates a fracture limit of the solid thin plate when the solid thin plate is subjected to the reference strain rate before the solid thin plate is fractured, and wherein the second fracture limit curve measured at said single reference strain rate is used as a fracture limit for fracture determination of the solid thin plate, and deformation conditions of the solid thin plate are evaluated by numerical analysis that employs a dynamic explicit method; and
converting a plastic strain of the solid thin plate, obtained by the dynamic explicit method, into a stress by a numerical simulation post-processing, and comparing said stress with the second fracture limit curve in stress space, to predict whether a fracture would occur in the solid thin plate and to provide the presence of the fracture occurrence in the solid thin plate for determining a material fracture in a crash process of the thin plate subjected to a press-forming procedure, to provide information associated with the fracture prediction for press-forming the automobile body part using the thin plate, wherein a hole expansion ratio is used as a criterion for a fracture.

23. The method for designing an automobile body part using a thin plate which includes a metal material as recited in claim 22, wherein
the second fracture limit curve in stress space does not depend on the deformation path of the solid thin plate, when the deformation path of the solid thin plate varies among a plurality of different deformation paths.

* * * * *